US012588898B2

(12) United States Patent
Ali et al.

(10) Patent No.: US 12,588,898 B2
(45) **Date of Patent: \*Mar. 31, 2026**

(54) ULTRASOUND IMAGING TECHNIQUES FOR SHEAR-WAVE ELASTOGRAPHY

(71) Applicants: GE Precision Healthcare LLC, Wauwatosa, WI (US); The General Hospital Corporation, Boston, MA (US)

(72) Inventors: Abder-Rahman Ali, Halifax (CA); Michael Wang, Wauwatosa, WI (US); Michael J. Washburn, Brookfield, WI (US); Yelena Tsymbalenko, Mequon, WI (US); Anthony E. Samir, Newton, MA (US); Viksit Kumar, Quincy, MA (US); Shuhang Wang, Newton, MA (US); Theodore Pierce, Auburndale, MA (US)

(73) Assignees: GE Precision Healthcare LLC; The General Hospital Corporation

( \* ) Notice: Subject to any disclaimer, the term of this patent is extended or adjusted under 35 U.S.C. 154(b) by 88 days.

This patent is subject to a terminal disclaimer.

(21) Appl. No.: 18/205,809

(22) Filed: Jun. 5, 2023

(65) Prior Publication Data

US 2024/0398382 A1     Dec. 5, 2024

(51) Int. Cl.
A61B 8/00 (2006.01)
G06T 7/00 (2017.01)
G06T 7/11 (2017.01)

(52) U.S. Cl.
CPC ............ A61B 8/5207 (2013.01); A61B 8/463 (2013.01); A61B 8/469 (2013.01); A61B 8/485 (2013.01);

(Continued)

(58) Field of Classification Search
CPC ................................ A61B 8/469; A61B 8/485
See application file for complete search history.

(56) References Cited

U.S. PATENT DOCUMENTS

| | | | | |
|---|---|---|---|---|
| 2011/0184292 A1* | 7/2011 | Yoo ...................... | A61B 8/5269 | |
| | | | 600/447 | |
| 2016/0143621 A1* | 5/2016 | Parthasarathy ........ | A61B 8/483 | |
| | | | 600/438 | |

(Continued)

FOREIGN PATENT DOCUMENTS

| | | | | |
|---|---|---|---|---|
| CN | 110353731 A | * 10/2019 | ............... | A61B 8/08 |
| JP | 2009195283 A | * 9/2009 | | |
| WO | 2013034878 A3 | 3/2013 | | |

OTHER PUBLICATIONS

Chen, T., Kornbligh S., Norouzi M., Hinton, G., 2020. A simple framework for contrastive learning of visual representations. Proceedings of the 37th International Conference on Machine Learning, PMLR119:1597:1607.

(Continued)

*Primary Examiner* — Anh Tuan T Nguyen
*Assistant Examiner* — Tommy T Ly
(74) *Attorney, Agent, or Firm* — MCANDREWS HELD & MALLOY, LTD

(57) ABSTRACT

By example, a method includes: receiving ultrasound image data of a patient, including a segmented region corresponding to a liver; automatically identifying an area for a region of interest within the segmented region, wherein the region (Continued)

of interest corresponds to a region in the liver for performing shear-wave elastography; and presenting, on a display, the ultrasound image data and the area for the region of interest.

13 Claims, 13 Drawing Sheets

(52) U.S. Cl.
CPC .............. *G06T 7/0012* (2013.01); *G06T 7/11* (2017.01); *G06T 2207/10132* (2013.01)

(56) References Cited

U.S. PATENT DOCUMENTS

| | | | | |
|---|---|---|---|---|
| 2019/0282211 | A1* | 9/2019 | Merritt | A61B 8/465 |
| 2020/0272841 | A1* | 8/2020 | Han | G06T 7/0012 |
| 2020/0367972 | A1* | 11/2020 | Zhang | A61B 90/37 |
| 2022/0202396 | A1* | 6/2022 | Cao | A61B 8/485 |
| 2022/0249061 | A1 | 8/2022 | Carrascal et al. | |
| 2023/0054588 | A1* | 2/2023 | Honarvar | A61B 8/5223 |
| 2024/0119705 | A1* | 4/2024 | Xu | G06V 10/50 |

OTHER PUBLICATIONS

Paszke, A., Chaurasia, A., Kim, S., Culurciello, E., 2016. ENet: A deep neural network architecture for real-time semantic segmentation. In: arXiv preprint arXiv: 1606:02147.

Katramados, I., Breckon, TP. 2011. Real-time visual saliency by division of gaussians. In 18th IEEE International Conference on Image Processing, pp. 1701-1704.

Farraioli, G., et al., 2015. WFUMB guidelines and recommendations for clinical use of ultrasound elastography: Part 3: liver. Ultrasound Med Biol.; 41(5):1161-79.

Redmon, J., Divvala, S., Girshick, R., Farhadi, A., 2016. You only look once: Unfiled, real-time object detection. In Proceedings of the IEEE conference on computer vision and pattern recognition 2016. pp. 779-778.

Ronneberger, O, Fischer, P, Brox, T. U-net: Convolutional networks for biomedical image segmentation. In Medical Image Computing and Computer-Assisted Intervention—MICCAI 2015: 18th International Conference, Munich, Germany, Oct. 5-9, 2015, Proceedings, Part III 18 2015 (pp. 234-241). Springer International Publishing.

* cited by examiner

300

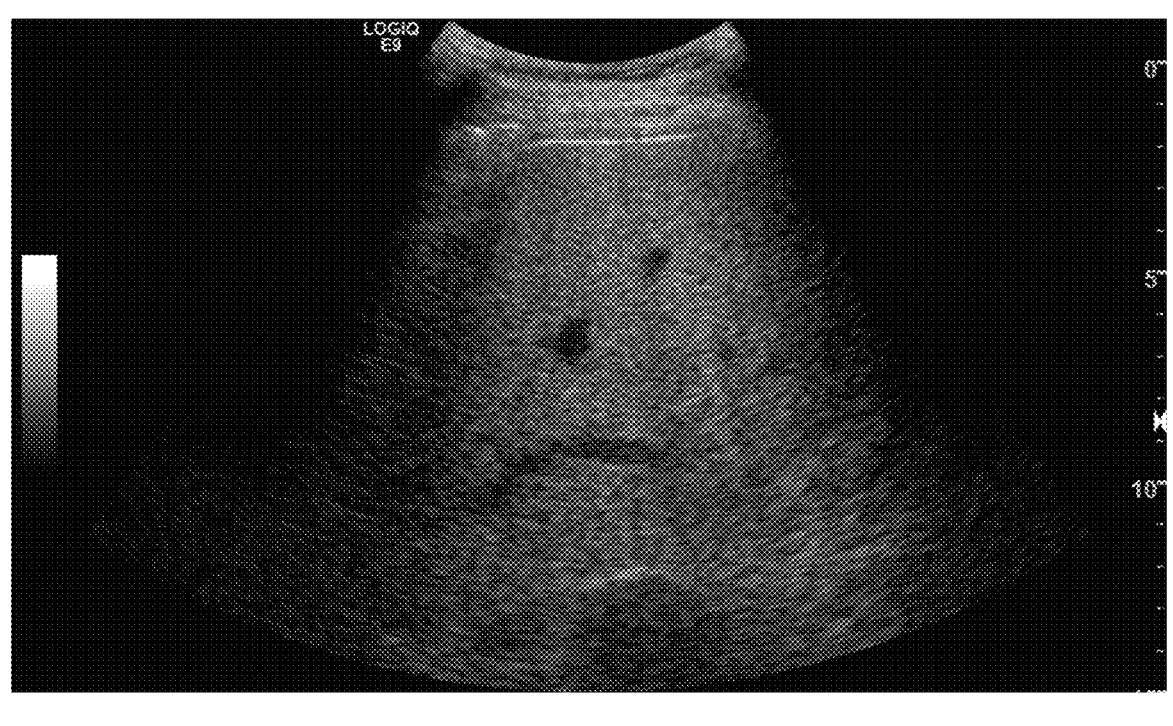
FIG. 4
1000
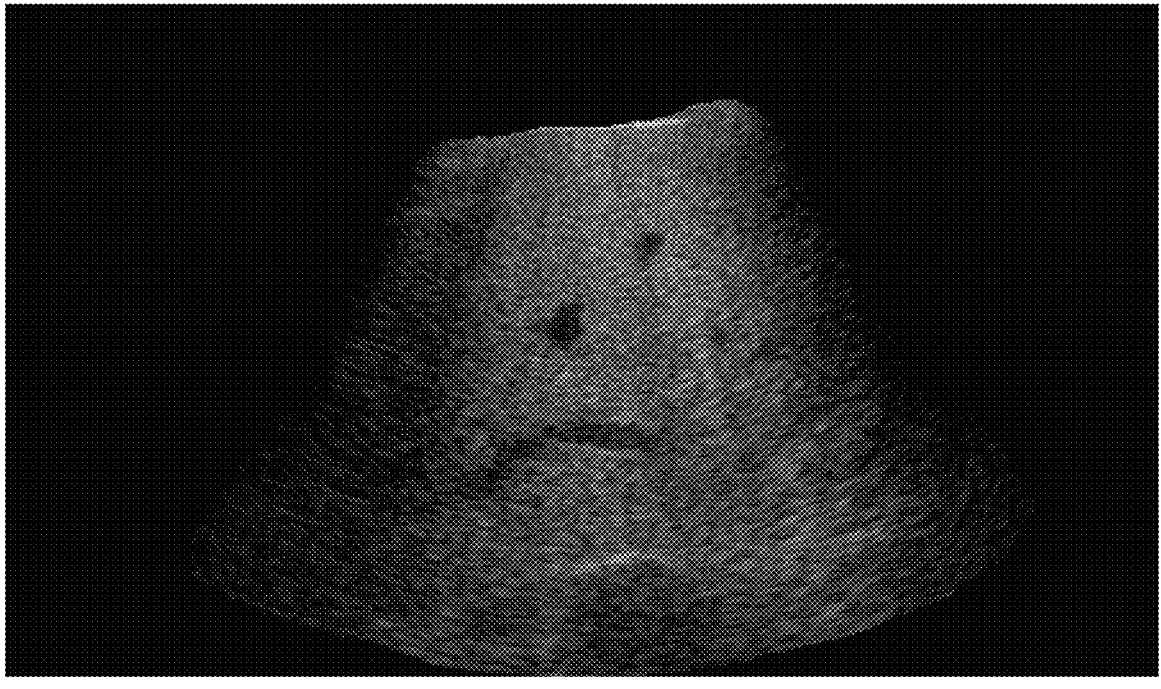
FIG. 5
1010

1020

1030

1040

1050

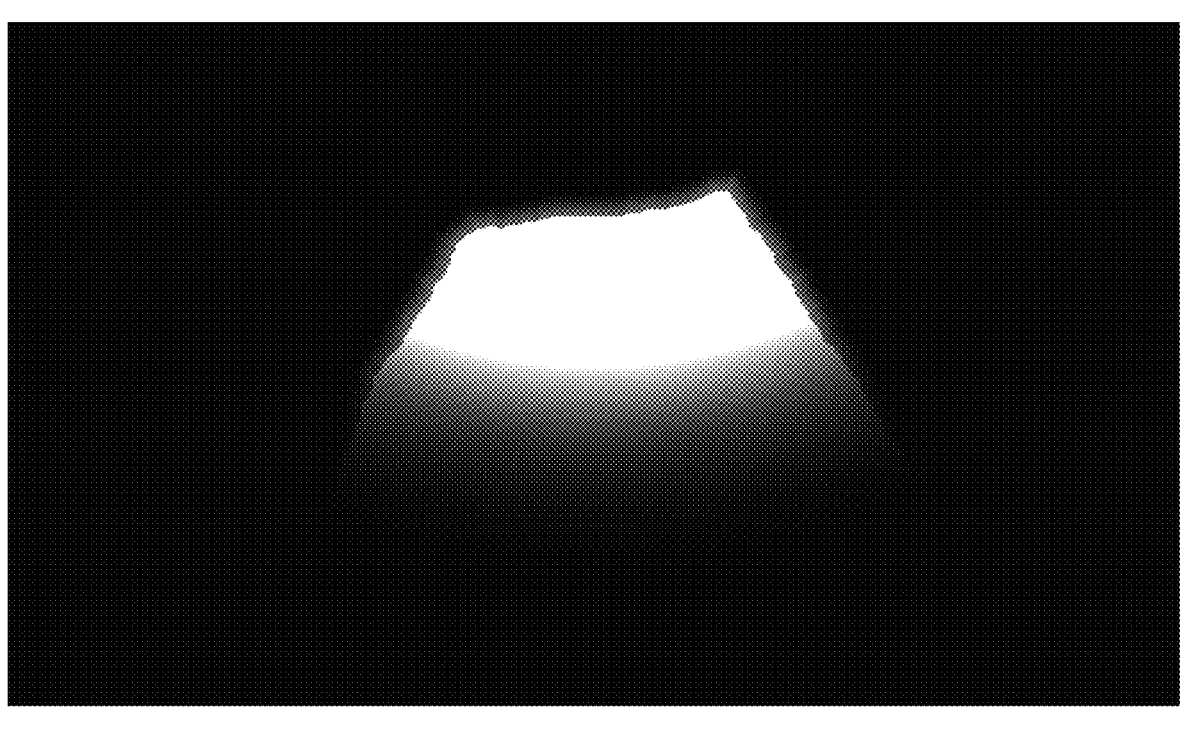
FIG. 10
1060
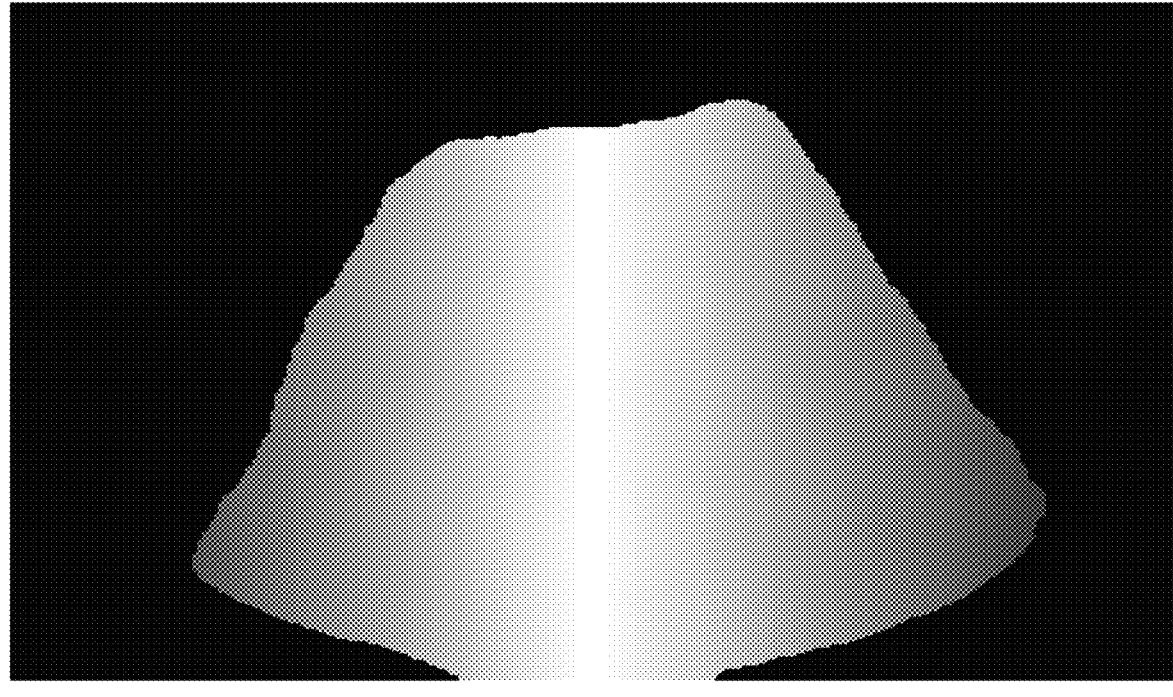
FIG. 11
1070

1080

1080

1090

1100

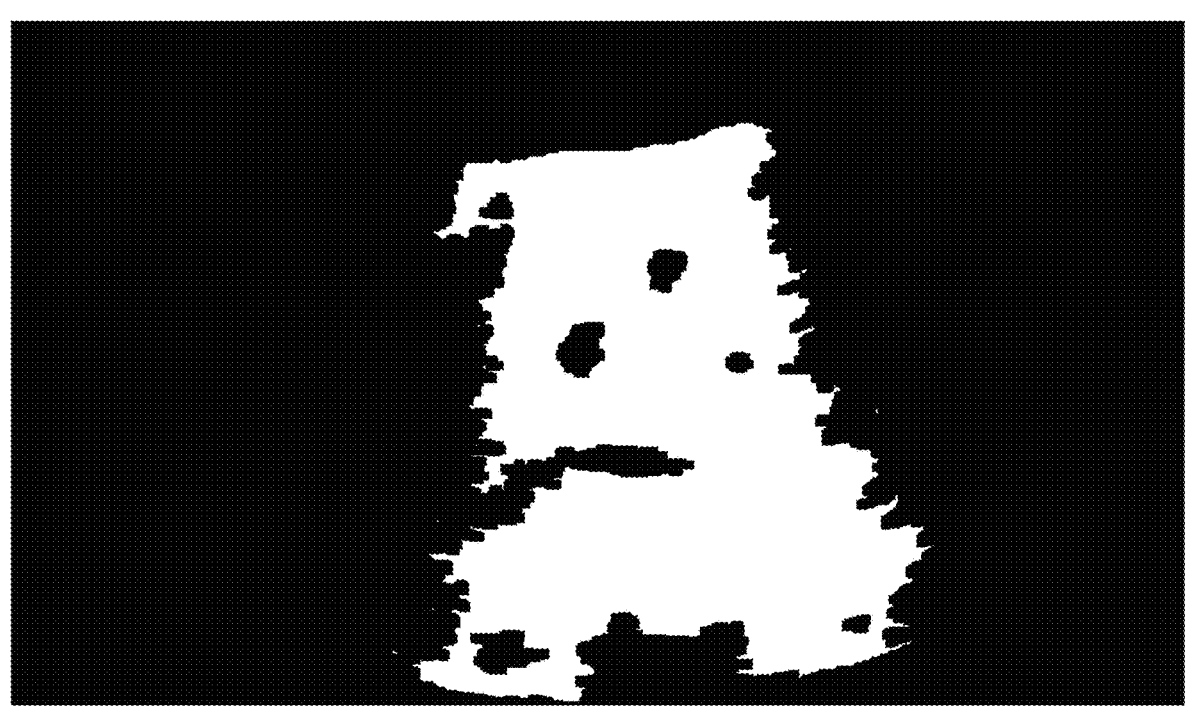
FIG. 15A
1052
FIG. 15B
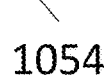
1054

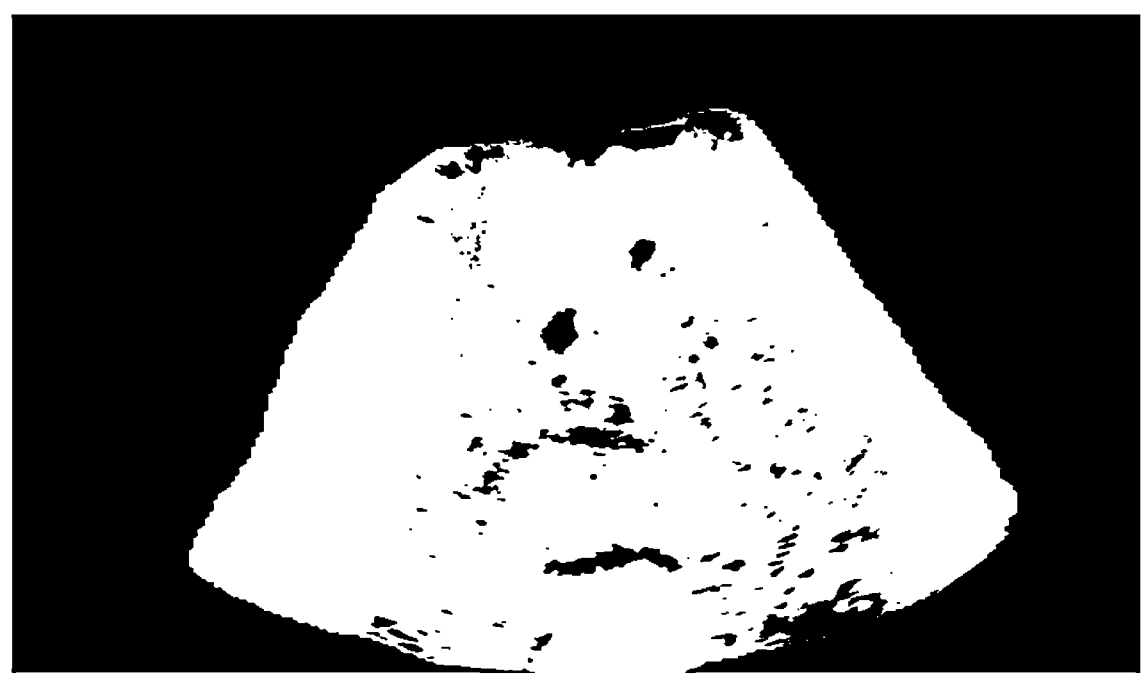
FIG. 15C
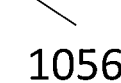
1056

1040

ULTRASOUND IMAGING TECHNIQUES FOR SHEAR-WAVE ELASTOGRAPHY

CROSS REFERENCE TO RELATED APPLICATIONS

[Not Applicable]

BACKGROUND

Generally, this application relates to ultrasound imaging and shear wave elastography. Non-alcoholic fatty liver disease (NAFLD), a cause of chronic liver disease, can be characterized or caused by the accumulation of excess fat in the liver, leading to damage and inflammation. Currently, there is upward trend in the incidence of NAFLD in the U.S., resulting in substantial medical costs. Liver biopsy can be used to diagnose NAFLD but it is invasive, relatively expensive, and may be subject to sampling error and interpretative variability. Due to these limitations, non-invasive alternatives have been developed, including ultrasound. As NAFLD progresses, liver stiffness increases, making it a biomarker. Shear wave elastography (SWE) is an ultrasound method, which can measure or estimate stiffness of liver tissue.

SUMMARY

According to embodiments, a method includes: receiving ultrasound image data of a patient, including a segmented region corresponding to a liver; automatically identifying an area for a region of interest within the segmented region, wherein the region of interest corresponds to a region in the liver for performing shear-wave elastography; and presenting, on a display, the ultrasound image data and the area for the region of interest. The method may further include segmenting the ultrasound image data to form the segmented region. The area for the region of interest may be the region of interest. The method may further include receiving an input to locate the region of interest within the area for the region of interest. The step of automatically identifying the area for the region of interest within the segmented region may further include: determining a first mask by filtering pixels that do not correspond to liver tissue; determining a second mask for identifying an axial position in the segmented region; determining a third mask for identifying a lateral position in the segmented region; and combining the first mask, the second mask, and the third mask to limit the area for the region of interest within the segmented region. The first mask may filter out pixels corresponding to at least one blood vessel in the liver. The first mask may filter out pixels corresponding to at least one hyperechoic region in the liver. The step of automatically identifying the area for the region of interest may further include: determining a fourth mask corresponding to image data in a region resulting from poor probe contact with the patient; and combining the first mask, the second mask, the third mask, and the fourth mask to limit the area for the region of interest within the segmented region. The method may further include performing shear-wave elastography to receive elasticity information from the region of interest in the liver. The method may further include: determining, in real-time, an angular, spatial relationship between the segmented region and an ultrasound probe; and presenting, on the display, a dynamic, real-time indicator corresponding to the angular, spatial relationship between the segmented region and the ultrasound probe.

According to embodiments, an ultrasound imaging system includes: a probe including at least one transducer configured to transmit ultrasonic waves and receive reflected ultrasonic waves; a display configured to present a presentation to an operator; and a processor configured to process data corresponding to the reflected ultrasonic waves to determine a segmented region corresponding to a liver of a patient, and further configured to cause the display to present the presentation, wherein the presentation includes image data of the segmented region and at least one dynamic region-of-interest indicator indicating a corresponding region of interest in the liver from which to process reflected ultrasonic shear waves to determine an elasticity of the liver. The system may further include a user interface, wherein the processor is configured to receive data from the user interface indicating a final location for the region of interest. The processor may further be configured to determine the region of interest by: determining a first mask by filtering pixels that do not correspond to liver tissue; determining a second mask for identifying an axial position in the segmented region; determining a third mask for identifying a lateral position in the segmented region; and combining the first mask, the second mask, and the third mask to limit an area for the region of interest within the segmented region. The first mask may filter out pixels that correspond to at least one blood vessel in the liver. The first mask may filter out pixels that correspond to at least one hyperechoic region in the liver. The processor may further be configured to determine the region of interest by: determining a fourth mask corresponding to image data in a region resulting from poor probe contact with the patient; and combining the first mask, the second mask, the third mask, and the fourth mask to limit the area for the region of interest within the segmented region. The presentation may further include an indicator of poor probe contact. The system may further comprising a shear-wave generator external to the probe to generate ultrasonic shear waves in the region of interest. The processor may further be configured to: determine, in real-time, an angular, spatial relationship between the segmented region and an ultrasound probe; and include, in the presentation, a dynamic indicator indicating, in real-time, the angular, spatial relationship between the segmented region and the ultrasound probe. The processor may further be configured to determine a distance between an epidermis contacting the probe and the segmented region.

BRIEF DESCRIPTION OF SEVERAL VIEWS OF THE DRAWINGS

FIG. 4 shows ultrasound image data.

FIG. 5 shows a segmented liver, according to embodiments.

FIG. 10 shows an axial distance mask, according to embodiments.

FIG. 11 shows a lateral distance mask, according to embodiments.

FIGS. 15A, 15B, and 15C show steps for generating a liver tissue mask, according to embodiments.

Figure 1:
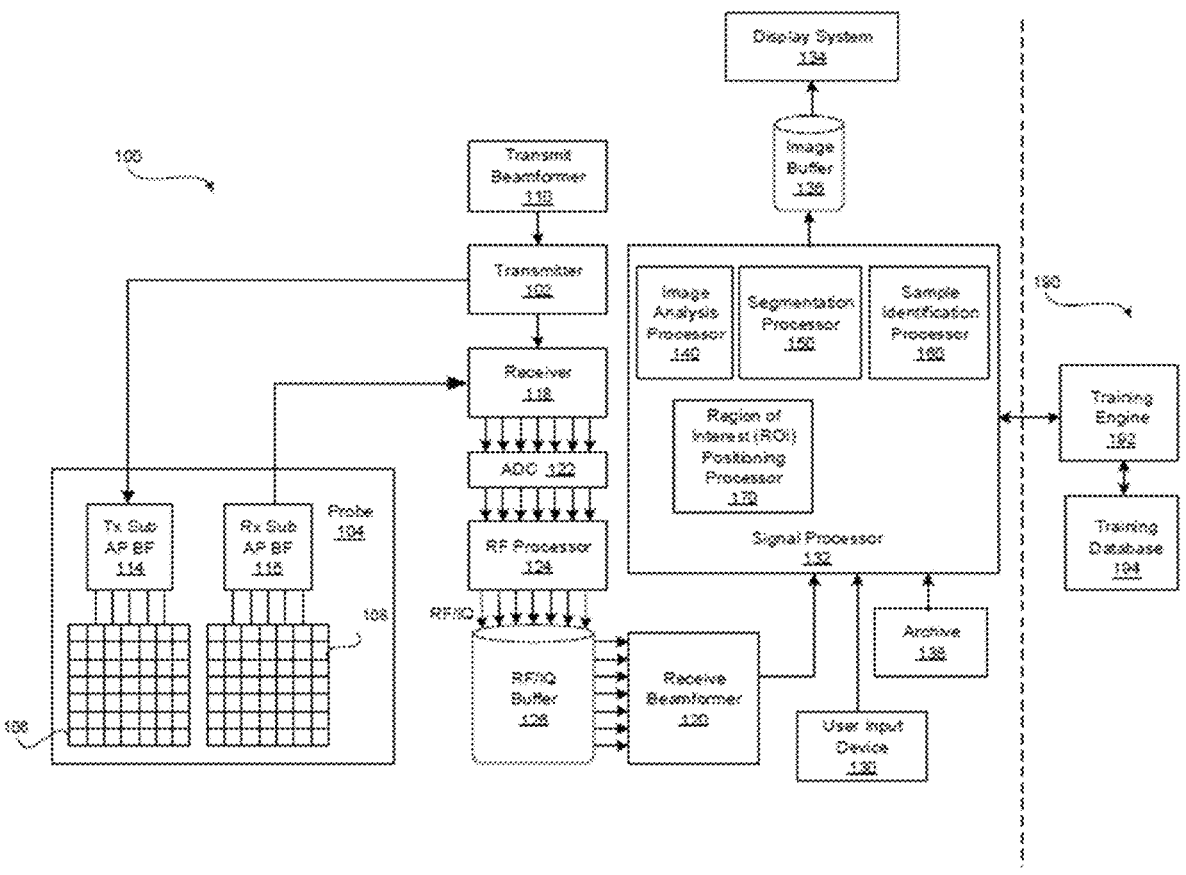
FIG. 1 illustrates an ultrasound system, according to embodiments.

The foregoing summary, as well as the following detailed description of certain techniques of the present application, will be better understood when read in conjunction with the appended drawings. For the purposes of illustration, certain techniques are shown in the drawings. It should be understood, however, that the claims are not limited to the arrangements and instrumentality shown in the attached drawings.

DETAILED DESCRIPTION

Disclosed herein are embodiments of ultrasonic methods and systems for identifying one or more regions of interest (herein, "region of interest" or "ROI" unless specified otherwise) in a liver of a patient and obtaining shear-wave elastography measurements from the region of interest. The region of interest may indicate a location in the liver from which to track the propagation of shear waves as part of a shear-wave elastography process. The propagation of these shear waves through the liver tissue in the region of interest may be analyzed to determine or estimate its stiffness. The region of interest may be automatically located or location may be facilitated through an automatic process. The region of interest may be located based on analyzing B-mode ultrasound image data (or other image data), in which the liver capsule or liver (herein, "liver" unless specified otherwise). Various aspects of the segmented liver image data may be assessed to locate the region of interest. Location of the region of interest may be completely automatic, or an operator may be provided one or more options for manually locating the region of interest. Embodiments herein also disclose determining and accounting for areas in the image data that correspond to poor probe contact with the patient's epidermis when locating the region of interest.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random-access memory, hard disk, or the like) or multiple hardware components. Similarly, the programs may be standalone programs, may be incorporated as subroutines in an operating system, may be functions in an installed software package, or the like. It should be understood that the various embodiments are not necessarily limited to the arrangements and instrumentality shown in the drawings. It should also be understood that embodiments may be combined as would be understood, or that other embodiments may be utilized and that structural, logical and electrical changes may be made without departing from the scope of the various embodiments. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" or "an embodiment" are not intended to be interpreted as excluding the existence of additional embodiments that also incorporate recited features. Moreover, unless explicitly stated to the contrary, embodiments "comprising" or "having" an element or a plurality of elements having a particular property may include additional elements not having that property.

Also as used herein, the term "image" or "image data" broadly refers to both viewable images and data representing a viewable image. Some embodiments generate (or are configured to generate) at least one viewable image. In addition, as used herein, the term "image" or "image data" is used to refer to an ultrasound mode such as B-mode, CF-mode, and/or sub-modes of B-mode and/or CF such as Shear Wave Elastography Imaging (SWEI), TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the calculations for the various embodiments, such as single or multi-core: CPU, Graphics Board, DSP, FPGA, ASIC or a combination thereof.

Various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams." Also, forming of images may be performed using channel combinations that may originate from more than one transmission event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments disclosed herein.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for automatically estimating a hepatorenal index (HRI) from ultrasound images.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

FIG. 1 is a block diagram of an exemplary ultrasound system 100 that is operable to segment a liver and automatically determine a region of interest therein, in accordance with various embodiments. Referring to FIG. 1, there is shown an ultrasound system 100 and a training system 190. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as a liver, or any suitable anatomical structure(s).

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select an examination type, select a desired ultrasound image view, select valid sample identification algorithms, reposition automatically-placed regions of interest, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, a touch pad, a trackball, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), an enterprise archive (EA), a vendor-neutral archive (VNA), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise an image analysis processor 140, a segmentation processor 150, a sample identification processor 160, and a region of interest (ROI) positioning processor 170. The signal processor 132 may be capable of receiving input information from a user input device 130 and/or archive 138, receiving image data, generating an output displayable by a display system 134, and manipulating the output in response to input information from a user input device 130, among other things. The signal processor 132, including the image analysis processor 140, the segmentation processor 150, the sample identification processor 160, and the region of interest (ROI) positioning processor 170, may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an image analysis processor 140 that comprises suitable logic, circuitry, interfaces and/or code that may be operable to analyze acquired ultrasound image data to determine whether a desired ultrasound image view has been obtained. For example, the image analysis processor 140 may analyze ultrasound image data acquired by an ultrasound probe 104 to determine whether a desired view, such any suitable ultrasound image view of the liver, has been obtained. The image analysis processor 140 may direct the signal processor 132 to freeze the view presented at the display system 134 once the desired image view is obtained. The view may be stored at archive 138 and/or any suitable data storage medium. The image analysis processor 140 may include, for example, artificial intelligence image analysis algorithms, one or more deep neural networks (e.g., a convolutional neural network such as ENet) and/or may utilize any suitable image analysis techniques or machine learning processing functionality configured to determine whether a desired view has been obtained. Additionally and/or alternatively, the artificial intelligence image analysis techniques or machine learning processing functionality configured to provide the image analysis techniques may be provided by a different processor or distributed across multiple processors at the ultrasound system 100 and/or a remote processor communicatively coupled to the ultrasound system 100. In various embodiments, the image analysis processor 140 may comprise suitable logic, circuitry, interfaces and/or code that may be operable to provide a quality metric associated with the obtained view. For example, the image analysis processor 140 may analyze the obtained ultrasound image view as a whole, regions of the obtained ultrasound image view, the obtained ultrasound image view segmented by the segmentation processor 150, or the like to provide a quality metric associated with the obtained view. The image analysis processor 140 may be configured to cause the display system 134 to present the quality metric with the obtained ultrasound image view. For example, the quality metric may be a score (e.g., 1, 2, 3, 4, 5), grade (e.g., A, B, C, D, F), rating (e.g., Excellent, Good, Fair, Poor), color-coding (e.g., green, yellow, red), or the like of the obtained ultrasound image view as a whole and/or for each region of the obtained ultrasound image view. The quality metric may assist a user in determining whether to proceed with the obtained view or to acquire additional ultrasound image data. The image analysis processor 140 may store the quality metric at archive and/or any suitable data storage medium.

The signal processor 132 may include a segmentation processor 150 that comprises suitable logic, circuitry, interfaces and/or code that may be operable to segment flow image frames and B-mode frames. The segmentation processor 150 may be used to identify a liver in the obtained ultrasound image view. In this regard, the segmentation processor 150 may include, for example, artificial intelligence image analysis algorithms, one or more deep neural networks (e.g., a convolutional neural network such as ENet) and/or may utilize any suitable form of artificial intelligence image analysis techniques or machine learning processing functionality configured to provide automated segmentation functionality. Additionally and/or alternatively, the artificial intelligence image analysis techniques or machine learning processing functionality configured to provide the automated segmentation may be provided by a different processor or distributed across multiple processors at the ultrasound system 100 and/or a remote processor communicatively coupled to the ultrasound system 100. For example, the image segmentation functionality may be provided as a deep neural network that may be made up of, for example, an input layer, an output layer, and one or more hidden layers in between the input and output layers. Each of the layers may be made up of a plurality of processing nodes that may be referred to as neurons. For example, the image segmentation functionality may include an input layer having a neuron for each sample or a group of samples from an obtained ultrasound image view of the liver and a kidney. The output layer may have a neuron corresponding to a plurality of pre-defined anatomical structures, such as a liver, a renal cortex, or any suitable anatomical structure. Each neuron of each layer may perform a processing function and pass the processed ultrasound image information to one of a plurality of neurons of a downstream layer for further processing. As an example, neurons of a first layer may learn to recognize edges of structure in the obtained ultrasound image. The neurons of a second layer may learn to recognize shapes based on the detected edges from the first layer. The neurons of a third layer may learn positions of the recognized shapes relative to landmarks in the obtained ultrasound image. The processing performed by the deep neural network may identify anatomical structures and the location of the structures in the obtained ultrasound image with a high degree of probability.

In an exemplary embodiment, the segmentation processor 150 may be configured to store the image segmentation information at archive 138 and/or any suitable storage medium. The segmentation processor 150 may be configured to cause the display system 134 to present the image segmentation information with the obtained ultrasound image. The image segmentation information may be provided to the image analysis processor 140 for providing a quality metric associated with the obtained ultrasound image view as discussed above. The image segmentation information may be provided to the sample identification processor 160 for identifying valid samples in the liver of the obtained ultrasound image, as described below.

Still referring to FIG. 1, the training system 190 may comprise a training engine 192 and a training database 194. The training engine 192 may comprise suitable logic, circuitry, interfaces and/or code that may be operable to train the neurons of the deep neural network(s) (e.g., artificial intelligence model(s)) inferenced (i.e., deployed) by the image analysis processor 140, segmentation processor 150, sample identification processor 160, and/or ROI positioning processor 170. For example, the artificial intelligence model inferenced by the image analysis processor 140 may be trained to automatically identify an ultrasound image view (e.g., a liver capsule). The artificial intelligence model inferenced by the segmentation processor 150 may be trained to automatically segment an obtained ultrasound image view to identify anatomies (e.g., a liver). As an example, the training engine 192 may train the deep neural networks deployed by the image analysis processor 140 and/or segmentation processor 150 using database(s). The ultrasound images may include ultrasound images of a particular anatomical feature, such as a liver, or any suitable ultrasound images and features.

In certain embodiments, the training engine 192 and/or training databases 194 may be remote system(s) communicatively coupled via a wired or wireless connection to the ultrasound system 100 as shown in FIG. 1. Additionally and/or alternatively, components or all of the training system 190 may be integrated with the ultrasound system 100 in various forms. In certain embodiments, the training system 190 may be separate from ultrasound system 100, and a model may be trained and then included in ultrasound system 100. For example, a model may be trained to segment a liver capsule or liver, and then the trained model may be included in ultrasound system 100, for example, as part of signal processor 132 or associated memory. Certain types of training are disclosed in U.S. Ser. No. 18/205,804, filed on Jun. 5, 2023, which is incorporated by reference in its entirety, herein.

Figure 2:
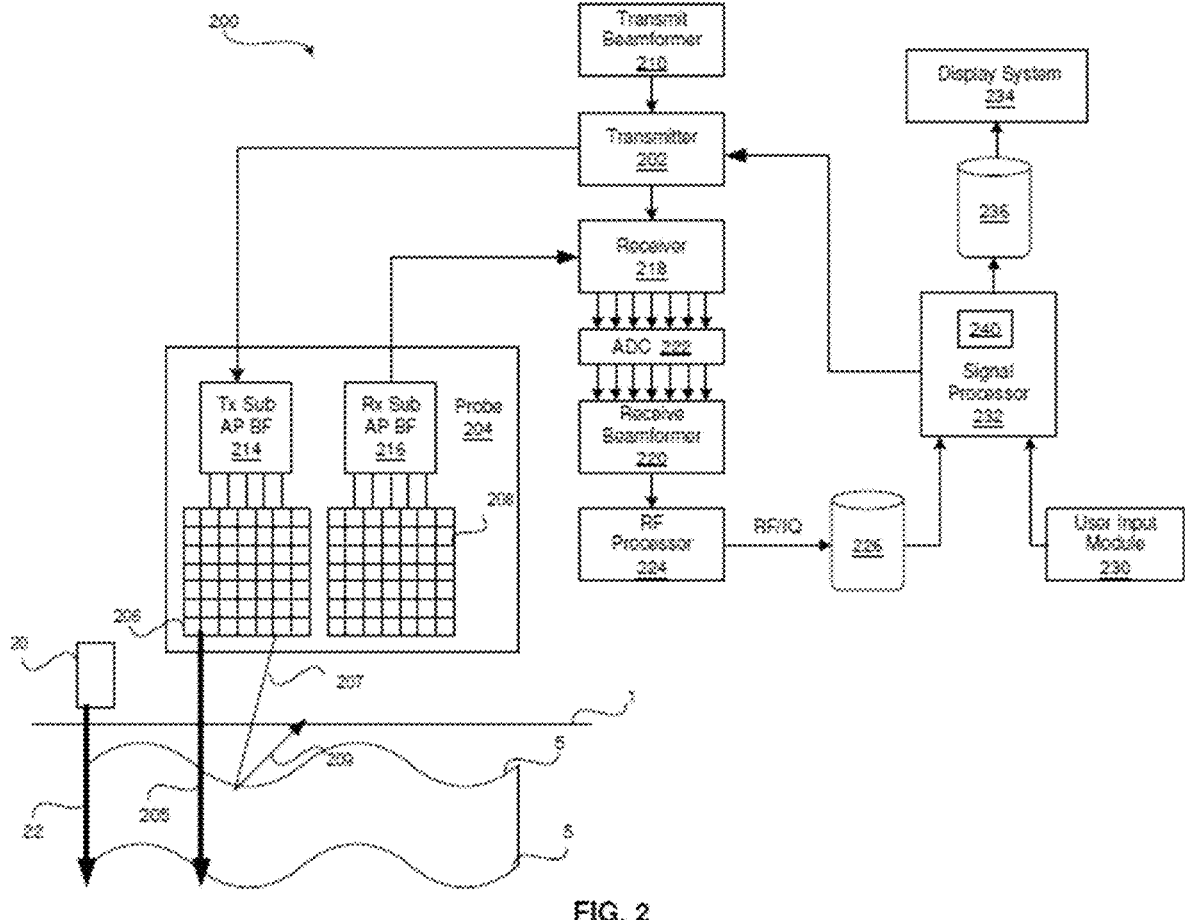
FIG. 2 illustrates an ultrasound system for performing shear-wave elastography, according to embodiments.

FIG. 2 shows a block diagram of an exemplary ultrasound system 200, which is operable to perform a shear-wave elastography process, for example, to obtain information about liver tissue in a region of interest. Ultrasound system 200 may be similar and/or share components with ultrasound system 100. For example, ultrasound system 200 and ultrasound system 100 may be integrated with each other. For example, there may only be one system that performs conventional ultrasound imaging and shear-wave elastography. FIG. 2 illustrates an ultrasound system 200 and a vibration device or transducer 20. The transducer 20 may be external to the ultrasound system 200. The transducer 20 may be configured to provide an external "push" force 22 to create shear waves 5 in a patient's tissue 1. As will be further discussed, the tissue 1 may be liver tissue or tissue or structure a proximate to the liver tissue. Additionally and/or alternatively, the ultrasound system 200 itself may provide a push force, such as a relatively high-intensity ultrasonic push pulse 205, for generating the shear waves 5 in the tissue 1. The ultrasound system 200 comprises a transmitter 202 (e.g., similar or the same as transmitter 102), an ultrasound probe (or "probe") 204 (e.g., similar or the same as probe 104), a transmit beamformer 210 (e.g., similar or the same as transmit beamformer 110), a receiver 218 (e.g., similar or the same as receiver 118), a receive beamformer 220 (e.g., similar or the same as receive beamformer 120), an RF processor 224 (e.g., similar or the same as RF processor 124), an RF/IQ buffer 226 (e.g., similar or the same as RF/IQ buffer 126), a user-input module 230 (e.g., similar or the same as user-input module 130), a signal processor 132 (e.g., similar or the same as signal processor 132), an image buffer 236 (e.g., similar or the same as image buffer 136), and a display system 234 (e.g., similar or the same as display system 134.

The transmitter 202 may comprise suitable logic, circuitry, interfaces and/or code that may be operable to drive transducer(s) an ultrasound probe 204. The ultrasound probe 204 may comprise a one dimensional (1D, 1.25D, 1.5D or 1.75D) array or two dimensional (2D) array of transducers, such as piezoelectric elements. The ultrasound probe 204 may comprise transmit transducer elements 106 and receive transducer elements 208, which may be completely coextensive, partially coextensive, or separate.

The transmit beamformer 210 may comprise suitable logic, circuitry, interfaces and/or code that may be operable to control the transmitter 202, which, through a transmit sub-aperture beamformer 214, drives the transmit transducer elements 206 to emit relatively high-intensity ultrasound push pulses 205 into a point of disturbance of the tissue 1 and to emit ultrasonic transmit signals 207 into a region of interest of the tissue 1. As used herein, the term "high-intensity ultrasound push pulses" refers to a derated spatial-peak temporal-average intensity (ISPTA.3) of between 200 and 700 mW/cm². The transmitted high-intensity ultrasound push pulses 205 may displace the tissue 1 to create shear waves 5 propagating laterally from the point of disturbance. The transmitted ultrasonic signals 207 may be reflected from structures, like the tissue 1 as deformed by the shear waves 5, to produce echoes 209. The echoes 209 are received by the receive transducer elements 208. The group of receive transducer elements 208 in the ultrasound probe 204 may be operable to convert the received echoes 209 into analog signals, undergo sub-aperture beamforming by a receive sub-aperture beamformer 216, and are then communicated to a receiver 218.

The receiver 218 may comprise suitable logic, circuitry, interfaces and/or code that may be operable to receive and demodulate the signals from the receive sub-aperture beam-former 216. The demodulated analog signals may be communicated to one or more of the plurality of A/D converters 222 (e.g., similar to A/D converters 122). The plurality of A/D converters 222 may comprise suitable logic, circuitry, interfaces and/or code that may be operable to convert the demodulated analog signals from the receiver 218 to corresponding digital signals. The plurality of A/D converters 222 are disposed between the receiver 218 and the receive beamformer 220. Notwithstanding, the invention is not limited in this regard. Accordingly, in some embodiments, the plurality of A/D converters 222 may be integrated within the receiver 218.

The receive beamformer 220 may comprise suitable logic, circuitry, interfaces and/or code that may be operable to perform digital beamforming processing on the signals received from the plurality of A/D converters 222. The resulting processed information may be converted back to corresponding RF signals. The corresponding output RF signals that are output from the receive beamformer 220 may be communicated to the RF processor 224. In accordance with some embodiments, the receiver 218, the plurality of A/D converters 222, and the beamformer 220 may be integrated into a single beamformer, which may be digital.

The RF processor 224 may comprise suitable logic, circuitry, interfaces and/or code that may be operable to demodulate the RF signals. In accordance with an embodiment, the RF processor 224 may comprise a complex demodulator (not shown) that is operable to demodulate the RF signals to form I/Q data pairs that are representative of the corresponding echo signals. The RF or I/Q signal data may then be communicated to an RF/IQ buffer 226.

The RF/IQ buffer 226 may comprise suitable logic, circuitry, interfaces and/or code that may be operable to provide temporary storage of the RF or I/Q signal data, which is generated by the RF processor 224.

The user-input module 230 may be utilized to initiate shear-wave elastography imaging, change scan mode, input patient data, surgical instrument data, scan parameters, settings, configuration parameters, and the like. In an exemplary embodiment, the user input module 230 may be operable to configure, manage and/or control operation of one or more components and/or modules in the ultrasound system 200. In this regard, the user-input module 230 may be operable to configure, manage and/or control operation of transmitter 202, the ultrasound probe 204, the transmit beamformer 210, the receiver 218, the receive beamformer 220, the RF processor 224, the RF/IQ buffer 226, the user-input module 230, the signal processor 232, the image buffer 236, and/or the display system 234. The user-input module 230 may be located at various positions on and/or around the ultrasound system 200 such as on the probe 204, at a control panel, and/or at any suitable location.

The signal processor 232 may comprise suitable logic, circuitry, interfaces and/or code that may be operable to process ultrasound information (i.e., RF signal data or IQ data pairs) for presentation on a display system 234. The signal processor 232 is operable to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the RF/IQ buffer 226 during a scanning session and processed in less than real-time in a live or off-line operation. In the exemplary embodiment, the signal processor 232 may comprise a shear wave elastography processing module 240.

The ultrasound system 200 may be operable to continuously acquire ultrasound information at a frame rate that is suitable for the imaging situation in question. Typical frame rates range from 20-70 fps but may be lower or higher. For example, shear-wave elastography imaging may have higher frame rates related to the high pulse-repetition frequency used to image shear waves 5 in tissue 1. In various embodiments, the pulse-repetition frequency in a shear-wave elastography imaging mode is at least 300 pulses/second, and preferably greater or equal to 1000 pulses/second. The acquired ultrasound information may be displayed on the display system 234 at a display-rate that can be the same as the frame rate, or slower or faster.

An image buffer 236 is included for storing processed frames of acquired ultrasound information that are not scheduled to be displayed immediately. Preferably, the image buffer 236 is of sufficient capacity to store at least several seconds worth of frames of ultrasound information. The frames of ultrasound information are stored in a manner to facilitate retrieval thereof according to its order or time of acquisition. The image buffer 236 may be embodied as any known data storage medium.

The shear-wave elastography processing module 240 may comprise suitable logic, circuitry, interfaces and/or code that may be operable to handle processing of shear wave ultrasound data to provide information about a region of interest, such as a region of interest in a liver. As used herein, the term "shear-wave ultrasound data" refers to ultrasound information received at the signal processor 232 corresponding with the received echoes 209 produced by the back-scattering of the transmitted ultrasonic signals 207 from structures (e.g., tissue 1) and surgical instruments in the object of interest as deformed by the shear waves 5. In this regard, the shear-wave elastography processing module 240 may comprise suitable logic, circuitry, interfaces and/or code that may be operable to handle processing the shear wave ultrasound data to determine a local distribution of shear wave speed in the tissue 1. The shear-wave speed may be computed by direct inversion of the Helmholtz equation, time-of-flight measurement, or any suitable computational method. The shear-wave ultrasound data may be acquired after a push disturbance is induced in the tissue 1 by the force of a focused ultrasound beam 205 or by an external push force 22, for example. The push disturbance 205, 22 generates shear waves 5 that propagate laterally from the point of disturbance. The ultrasound system 200 acquires the shear-wave ultrasound data using a high pulse repetition frequency. As used herein, the term "high-pulse repetition frequency" refers to a pulse repletion frequency of at least 300 pulses/second. In a preferred embodiment, the pulse repetition frequency used to acquire shear-wave ultrasound data is greater or equal to 1000 pulses/second.

The shear wave elastography processing module 240 may comprise suitable logic, circuitry, interfaces and/or code that may be operable to convert the local distribution of shear wave speed in the tissue 1 to a map, such as a velocity distribution map, an elasticity map, a spatial gradient map, or any suitable map representing the contrast between the needle 10 and surrounding tissue 1. For example, the local distribution may be mapped based on the shear-wave speed to generate a velocity distribution map. As another example, the local distribution may be converted to the elasticity map by computing the stiffness based on Young's modulus, a similar shear modulus, or any suitable conversion computation. Moreover, in various embodiments, a spatial gradient filter may be applied to the velocity distribution map and/or elasticity map to generate a spatial gradient map providing enhanced visualization tissue of interest.

The map represents the speed that the shear wave passed through the tissue at lateral locations from the point of disturbance in the shear-wave ultrasound data. The shear-wave propagation velocity corresponds to the stiffness of the tissue at the lateral locations. Specifically, the higher shear-wave velocity corresponds with more stiffness and the lower shear-wave velocity corresponds with less stiffness. Based on the difference in velocity and/or elasticity of tissue (e.g., region of interest of a liver), the stiffness of the liver can be assessed. For example, the maps may be color-coded or grayscale maps having a range of colors or grays that correspond with the shear-wave speed and/or elasticity. Specifically, an elasticity map may have dark blue or dark gray/black corresponding with soft elasticity to red or light gray/white corresponding with hard elasticity, among other things. The map having the elasticity information may be overlaid on an ultrasound image such as a B-mode image or any suitable ultrasound image.

Additionally and/or alternatively, the shear-wave elastography processing module 240 may comprise suitable logic, circuitry, interfaces and/or code that may be operable to perform image segmentation. In various embodiments, the shear-wave elastography processing module 240 may perform the image segmentation semi-automatically or automatically.

Figure 3:
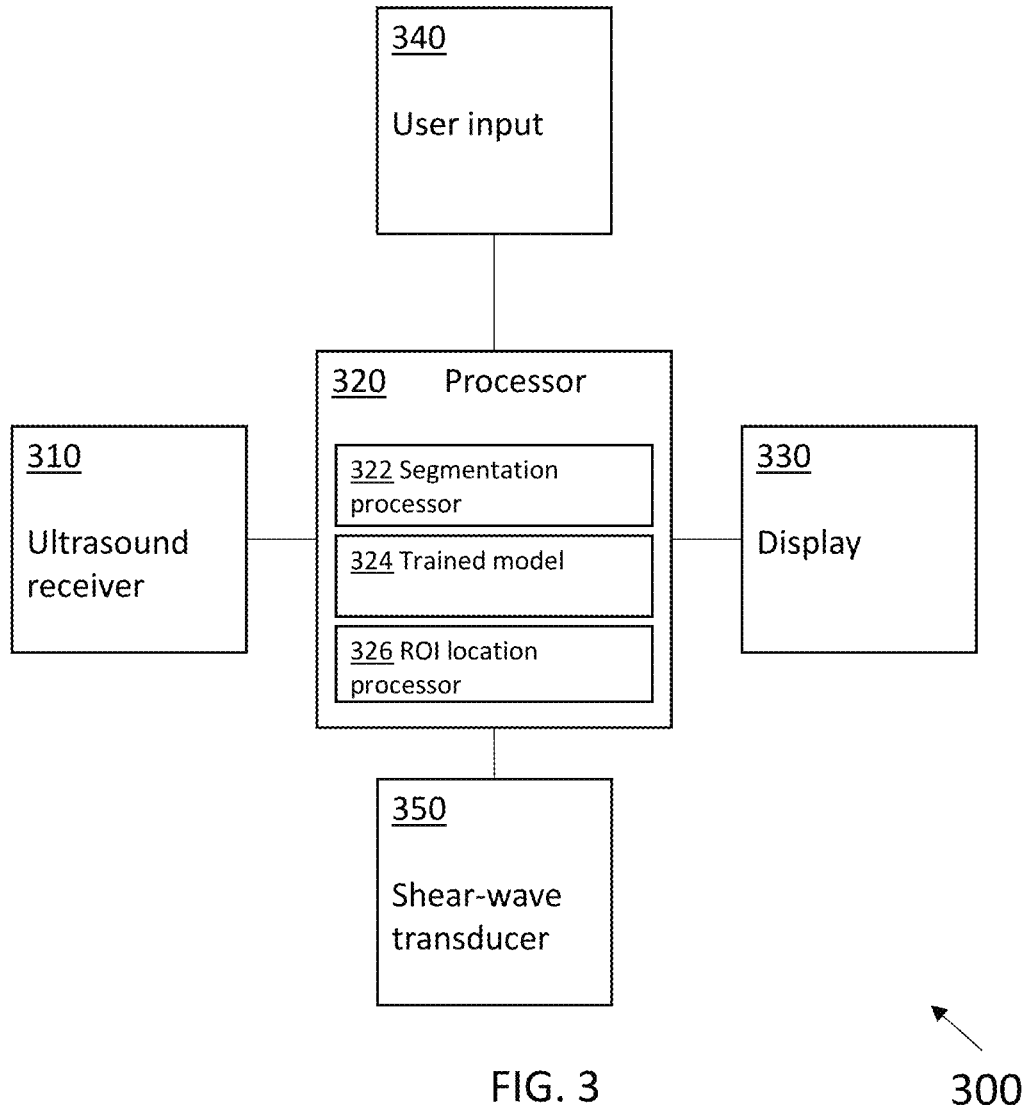
FIG. 3 illustrates an ultrasound imaging system, according to embodiments.

FIG. 3 illustrates an ultrasound imaging system 300, which may be similar or identical to ultrasound system 100 and/or ultrasound system 200. Ultrasound imaging system 300 may be a system that performs both conventional ultrasound imaging and obtains shear-wave elastography measurements (e.g., measurements convertible into image data or to determine other characteristics of human anatomy, such as liver stiffness related to non-alcoholic fatty liver disease). Thus ultrasound imaging system 300 may be a combination of ultrasound system 100 and ultrasound system 200 (or components thereof), and there may only be one system.

Ultrasound receiver 310 may include various components for receiving conventional ultrasound data and/or shear-wave elastography data. Ultrasound receiver 310 may receive signals from a probe (e.g., probes 104, 204) and may convert those signals to signals processable by processor 320. Components of ultrasound receiver 310 may include receiver (e.g., receivers 118, 218), A/D converter (e.g., A/D converters 122, 222), RF processor (e.g., RF processors 124, 224), RF/IQ buffer (e.g., RF/IQ buffers 126, 226), or receive beamformer (e.g., receive beamformer 120, 220). Ultrasound receiver 310 may provide ultrasound image data or shear-wave elastography measurements to processor 320.

Processor 320 may perform processing operations discussed below with respect to FIGS. 4-16. Processor 320 may be one processor or a plurality of processors, either grouped together (e.g., in one ASIC) and/or distributed remotely in different packages. Processor 320 may receive information from ultrasound receiver 310 that is ultrasound image data or can be converted by processor 320 into ultrasound image data. Processor may include functionality such as that disclosed with respect to signal processors 132, 232. Processor 320 may include segmentation processor 322, trained model 324, and ROI location processor 326, discussed below. Segmentation processor 322 may include functionality similar to, or inclusive of certain functionality as segmentation processor 150. Segmentation processor 322 may operate to segment a liver capsule or liver in ultrasound image data.

Segmentation processor 322 may work with trained model 324 stored in processor or in associated memory to segment anatomical structures in ultrasound image data. Segmentation processor 322 may also segment non-anatomical features, such as regions where data is obtained with poor probe contact. ROI location processor 326 may be similar to, or include certain functionality of ROI positioning processor 170.

Processor 320 may receive signals from user input 340 to control ultrasound imaging system 300. Processor 320 may cause information, such as a presentation, to be presented or displayed on display 330. Processor 320 may cause operation of shear-wave transducer 350, for example, as a process to gather shear-wave elastography measurements from a region of interest of a patient's liver to measure the stiffness of the liver.

Display 330 may be similar to display systems 134, 234. Display 330 may be used to present ultrasound image data and associated presentations as discussed herein. User input 340 may be similar to user input devices 130, 230. Shear-wave transducer 350 may be similar to transducer 20 and/or transducer elements 206.

FIGS. 4-15 depict image data and masks used for image processing, and for identifying a region of interest in a patient's live from which to evaluate shear-wave elastography measurements. These figures are described with respect to system 300, but this is for exemplary purposes only. Similar or identical components in systems 100 and 200 (or other ultrasound systems) can also be used to generate image data and perform processing, as will be understood.

FIG. 4 depicts ultrasound image data 1000, which may be obtained using ultrasound receiver 310. As shown, ultrasound image data 1000 includes B-mode data, which is 1055×616 pixels with an 8-bit grayscale depth. Ultrasound image data 1000 may be scaled before or during processing of the data. For example, ultrasound image data 1000 may be scaled to 224×224 pixels before performing some of the image processing techniques described herein.

Ultrasound image data 1000 may be scaled multiple times. For example, ultrasound image data 1000 may be scaled back to an original size (e.g., 1055×616 pixels) after certain image processing operations. As explained herein, other types of ultrasound image data 1000 may be used with the techniques described herein, but for exemplary purposes ultrasound image data 1000 is provided. Ultrasound image data 1000 includes image data of a patient's liver (and structures or features therein), as well as skin. An ultrasound probe (e.g., probes 104, 204) was used to generate ultrasound image data 1000. Ultrasound probe was located at the curved region at the top of ultrasound image data 1000 during image acquisition. Ultrasound image data 1000 may be stored in memory.

FIG. 5 depicts segmented liver 1010 extracted from ultrasound image data 1000. Segmented liver 1010 corresponds to the patient's liver, as shown in ultrasound image data 1000. Segmented liver 1010 may be determined by processor 320, which may process ultrasound image data 1000. Processor 320 may determine segmented liver 1010 using segmentation processor 322 in conjunction with trained model 324. Trained model 324 may have been previously trained, for example, as described by U.S. Ser. No. 18/205,804, filed on Jun. 5, 2023, the entirety of which is herein incorporated by reference. Segmentation processor 320 may execute inference instructions to process ultrasound image data 1000 using trained model 324. Segmentation processor 322 may determine segmented liver 1010 substantially in real-time when ultrasound image data 1000 is generated. For example, segmented liver 1010 may be determined within between 0.5 and 2 seconds (without limitation) after ultrasound image data 1000 is obtained. Segmented liver 1010 may be determined with segmentation processor 322 by other techniques that are not based on machine learning, such as clustering, region growing, level set, or watershed transformation, for example.

Figures 6, 7:
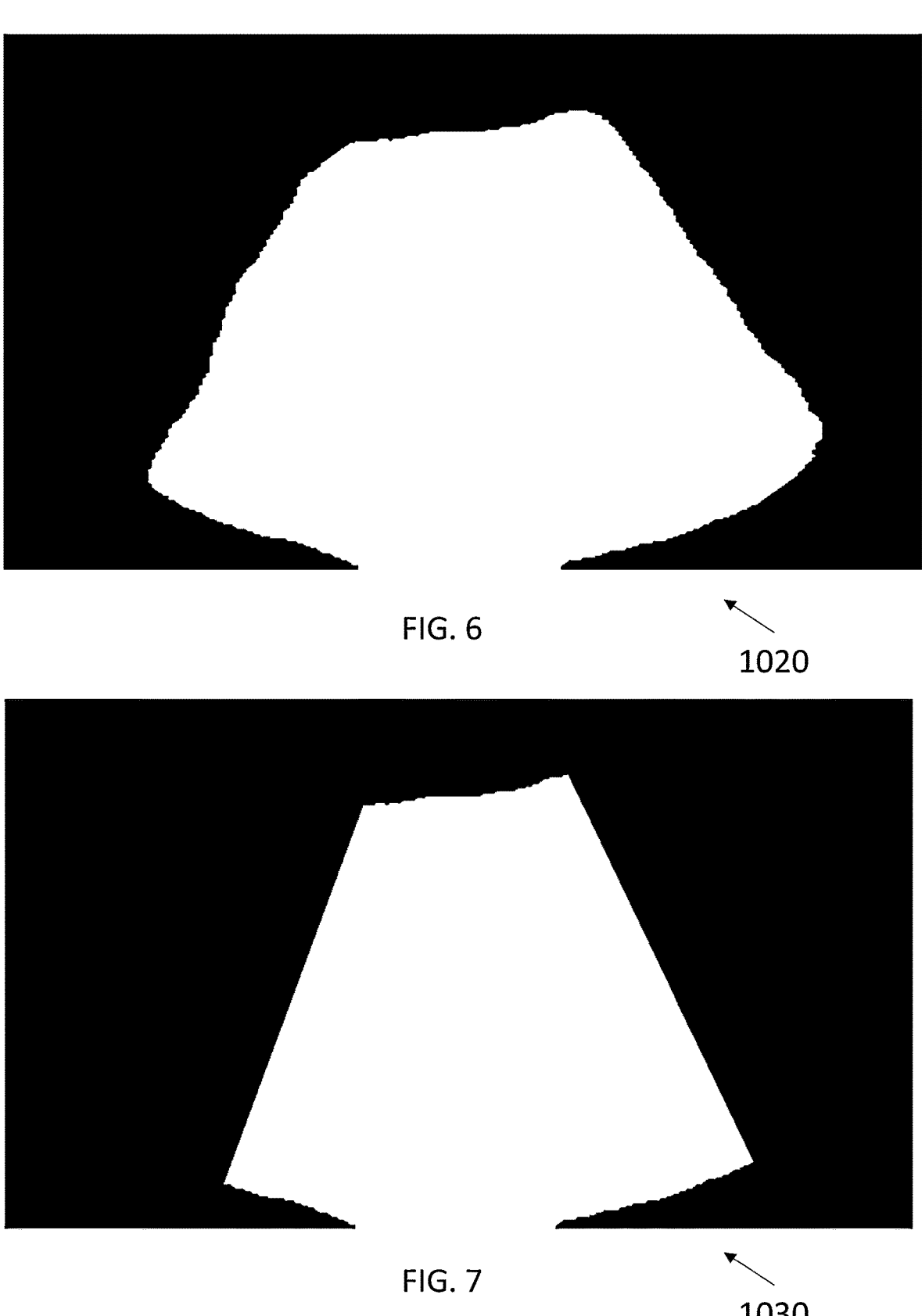
FIG. 6 shows a segmented liver mask, according to embodiments.
FIG. 7 shows a poor-probe-contact mask, according to embodiments.

The processes discussed with respect to FIGS. 6-16 may be performed, at least in part, by ROI location processor 326. FIG. 6 shows segmented liver mask 1020, which corresponds to segmented liver 1010. As shown, segmented liver mask 1020 has the same outer contour as segmented liver 1010. Regions of segmented liver mask 1020 within the outer contour are white, while regions exterior to the outer contour are black. As will be further discussed, black regions of segmented liver mask 1020 are used to filter out corresponding pixels in ultrasound image data 1000. Segmented liver mask 1020 may be determined or generated by ROI location processor 326 or segmentation processor 322. Segmented liver mask 1020 may be used as part of a process to locate a region of interest in the liver, from which to analyze shear-wave elastography data. Other masks described herein may also be used as part of this process.

FIG. 7 shows poor-probe-contact mask 1030, which is determined from ultrasound image data 1000. Poor-probe-contact mask 1030 may be designed to filter out regions in which data has been gathered even though there is poor contact between the probe (e.g., probe 104 or probe 204) and the patient. Poor probe contact refers to insufficient or improper contact between the ultrasound probe and the patient's skin, which can lead to suboptimal ultrasound images, affecting the quality of diagnosis or treatment. Poor probe contact may result in less reliable data, and poor-probe-contact mask 1030 may reduce error in processing such less-reliable data by removing that data (e.g., not processing that data). Poor-probe-contact mask 1030 may be determined or generated by processor 320 when processing ultrasound image data 1000. Processor 320 may determine poor-probe-contact mask 1030 using segmentation processor 322, for example, in combination with trained model 324. Processor 320 may execute inference instructions to process ultrasound image data 1000 using segmentation processor 322 and trained model 324. Examples of training and use of segmentation processor 322 and trained model 324 for poor-probe-contact masks 1030 are discussed in U.S. Ser. No. 18/205,804, filed on Jun. 5, 2023, the entirety of which is incorporated by reference herein. Segmentation processor 322 may determine segmented liver 1010 (or segmented liver mask 1020) and poor-probe-contact mask 1030 substantially simultaneously. According to embodiments, poor-probe-contact mask 1030 is adapted from segmented liver mask 1020. According to embodiments, the top and bottom contours of poor-probe-contact mask correspond to the top and bottom contours of segmented liver mask 1020. According to embodiments, the lateral sides of poor-probe-contact mask 1030 are determined according to angles $\theta_1$ and $\theta_2$ as disclosed in FIGS. 16, 17 and corresponding text. For example, a line defined by $\theta_1$ as described in FIGS. 16, 17 may correspond to the left side of poor-probe-contact mask. For example, a line defined by $\theta_2$ as described by FIGS. 16, 17 may correspond to the right side of poor-probe-contact mask. As shown in FIG. 7, the black region outside of the contour of poor-probe-contact mask 1030 corresponds to pixels in ultrasound image data 1000 that will be filtered out due to issues of poor probe contact with the patient (e.g., patient's skin).

Figure 8:
FIG. 8 shows a poor-probe-contact artifact mask, according to embodiments.

FIG. 8 shows poor-probe-contact artifact mask 1040, which is determined from ultrasound image data 1000. The poor-probe-contact artifact mask 1040 may be black and white, and may represent one or more locations where contact between the ultrasound probe and the skin is not sufficient. These locations can appear at various positions in ultrasound image data 1000, for example, due to a curved nature of a probe. They may appear on the top left, top right, or both areas of ultrasound image data 1000. The features in poor-probe-contact artifact mask 1040 may have a height that is greater than the thickness of the patient's skin. Ultrasound image data 1000 is constructed from sound-wave data collected by a transducer. The sound-wave data includes the amplitude, frequency, and the time it takes for the ultrasound signal to return to the transducer. The image is then constructed in a way that represents the depth of the tissue, creating a "height" in the image data, even though poor probe contact occurs at the skin surface. So, when the probe's contact with the skin is poor, the echo waves may be affected, creating artifacts that can affect the image in terms of depth, thus giving the artifact a "height" within the image. Poor-probe-contact artifact mask 1040 may be combined with poor-probe-contact mask 1030. As described herein, poor-probe-contact mask 1030 and poor-probe-contact artifact mask 1040 may be considered as part of the same mask, and may be referred to as just poor-probe-contact mask 1030. Poor-probe-contact artifact mask 1040 may be determined with segmentation processor 322 in combination with trained model 324. Processor 320 may execute inference instructions to process ultrasound image data 1000 using segmentation processor 322 and trained model 324. Examples of training and use of segmentation processor 322 and trained model 324 for poor-probe-contact artifact masks 1040 are discussed in U.S. Ser. No. 18/205,804, filed on Jun. 5, 2023, the entirety of which is incorporated by reference herein. Segmentation processor 322 may determine segmented liver 1010 (or segmented liver mask 1020) and poor-probe-contact artifact mask 1040 substantially simultaneously. Additional disclosure about poor-probe contact determination from poor-probe-contact artifact mask 1040 is provided in FIGS. 16, 17 and corresponding text. Additional disclosure about poor-probe-contact mask 1030 determination from poor-probe-contact artifact mask 1040 is provided in the context of FIGS. 7, 16, 17.

One or more poor-probe-contact artifacts (types of segments) in mask 1040 may exist. For example, one poor-probe-contact artifact appear on the left side of the centerline of ultrasound image data 1000, and one may appear on the right side of the centerline of ultrasound image data 1000. If poor-probe-contact artifacts exist, then corresponding indicators 1104 may be determined and displayed. Embodiments of such a process are further disclosed in FIGS. 14, 16, 17 and corresponding text.

Figure 9:
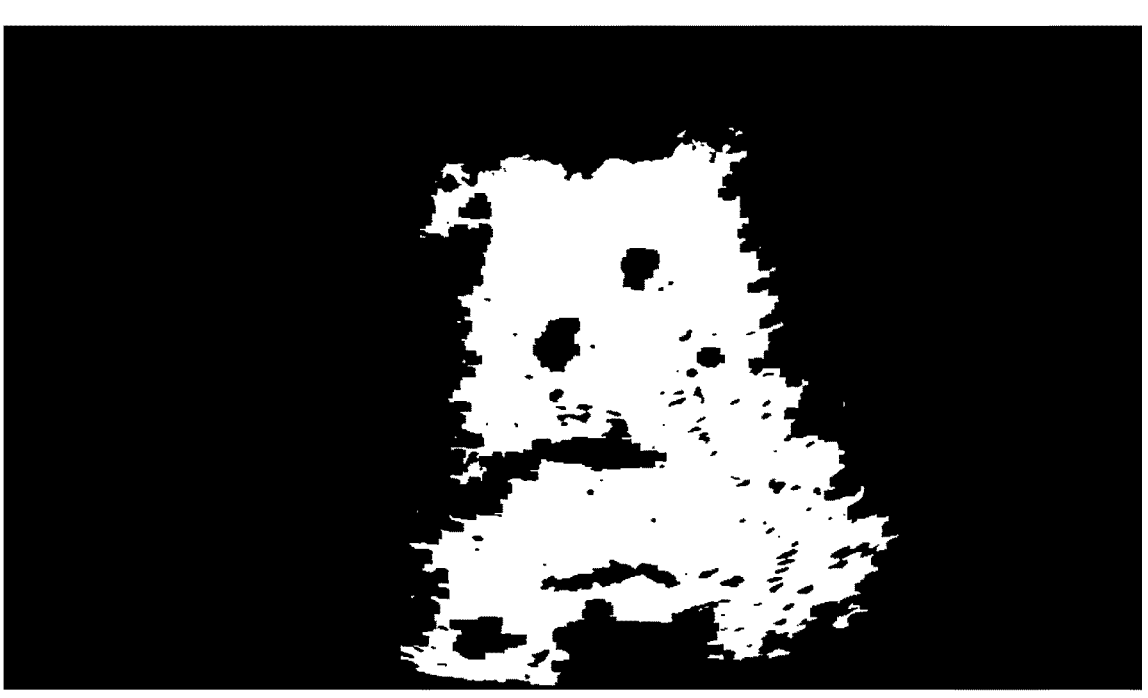
FIG. 9 shows a liver tissue mask, according to embodiments.

FIG. 9 shows a liver tissue mask 1050 which is determined from ultrasound image data 1000, and may optionally be limited to segmented liver 1010. In the embodiment as shown, liver tissue mask 1050 is determined with respect to ultrasound image data 1000, and not just segmented liver 1010. In embodiments, and as shown, liver tissue mask 1050 corresponds to the region that is not excluded by poor-probe-contact mask 1030, but liver tissue mask 1050 may be generated for the entire segmented liver 1010. Liver tissue mask 1050 may be determined or generated by processor 320, for example, using ROI location module 326. Liver tissue mask 1050 is used to filter out pixels in ultrasound image data 1000 that are within segmented liver 1010, but do not correspond to liver tissue. Examples of such structures or features include blood vessels and hyperechoic regions. Examples of hyperechoic regions include fat, calcifications (deposits of calcium in the tissue), or fibrosis (scar tissue that forms when the liver tries to heal itself after injury). For example, hyperechoic regions may occur where pockets of air or gas occur. Where there is an interface between fluid or tissue and air, for example, a relatively large amount of ultrasonic energy will be reflected. Such regions may correspond to features that are not liver tissue, even though they may be located within the liver. Liver tissue mask 1050 excludes such structures or features, such that clinical inquiries can focus on liver tissue itself (e.g., determining the stiffness of the liver by using shear-wave elastography measurements). Such structures or features may be determined by various techniques, including those described in context of FIGS. 15A-15C.

FIGS. 15A, 15B, and 15C show steps for generating liver tissue mask 1050, and may be generated or performed by processor 320, for example, using ROI location processor 326. Step 1052 is a type of mask, and it relates to, at least, filtering out blood vessels located in the liver. In embodiments, and as shown, mask 1052 excludes regions where image data corresponds to poor probe contact (e.g., poor-probe-contact mask 1030 has been applied to ultrasound image data 1000, or optionally only segmented liver 1010 before determining mask 1052). However, mask 1052 may be determined for the entire segmented liver 1010 or ultrasound image data 1000. To determine pixels in ultrasound image data 1000 that are likely to correspond to liver tissue, one or more thresholds may be applied to pixel brightness. For example, there may be a low threshold for pixel brightness, below which any pixel is excluded. Similarly, there may also be a high threshold for pixel brightness, above which any pixel is excluded. Thresholds may be absolute numbers, or they may be percentiles or some other measure. As one example, there is only a low threshold, and it is 10% (percentile). In this case, the darkest 10% of pixels will be filtered out.

After filtering out pixels by brightness threshold, a local difference threshold is assessed as part of step 1052. This comparison may be used to determine edges of blood vessels. For each pixel (or a subset thereof) in ultrasound image data 1000, a given pixel's brightness may be compared to nearby pixels. For example, a pixel's brightness may be compared to nearby pixels within a square area of size 45×45 pixels, where the given pixel is in the center of the square area. Relatively large differences may indicate the edge of a blood vessel. If differences are outside of an acceptable range (e.g., greater than a high threshold and/or lesser than a low threshold), then those pixels may be filtered out. Threshold may be an absolute number or some other measure, like percentile. For example, pixels may be filtered out when the differences are in the lowest 10% percentile.

In addition to step 1052, additional steps may be performed to determine liver tissue mask 1050, including step 1054 (FIG. 15B) and step 1056 (FIG. 15C). Steps 1054, 1056 relate to filtering out hyperechoic pixels in ultrasound image data 1000. In embodiments, and as shown, steps 1054, 1056 include regions where image data corresponds to poor probe contact (e.g., poor-probe-contact mask 1030 has not been applied to ultrasound image data 1000 or segmented liver 1010 before performing steps 1054, 1056). However, steps 1054, 1056 may be performed on only segmented liver 1010 that has been filtered by poor-probe-contact mask 1030. Step 1054 is a saliency map determined from ultrasound image data 1000. The pixel intensities in saliency map 1054 represent the saliency (i.e., distinctiveness) of the corresponding regions in the original image, rather than their intensity or brightness. This may be viewed as converting the original pixel intensities into a new quantity (i.e., saliency) rather than scaling those intensities. Saliency may be determined by a variety of techniques, including spectral residual approach, Itti Koch saliency model, Graph-Based Visual Saliency (GBVS), Boolean Map-based Saliency (BMS) model, or Division of Gaussians (DIVoG/DoG) saliency detection techniques. Step 1054, in this example, was determined using DIVoG/DoG saliency detection techniques. After generating saliency map 1054, a threshold may be applied to filter out areas of high saliency, resulting in step 1056, which is a type of mask. Such a threshold may be determined to effectively detect and avoid hyperechoic regions, which may have relatively high distinctiveness in ultrasound images. In this way, regions of lower saliency may be emphasized, and such regions may represent liver tissue, and not hyperechoic regions.

The masks 1052 and 1056 may be combined (e.g., multiplied with each other) to arrive at liver tissue mask 1050 shown in FIG. 9. Thus, liver tissue mask 1050 may filter out structures such as blood vessels and hyperechoic regions in the liver. However, liver tissue mask 1050 may be generated or designed to identify non-liver tissue (or liver tissue) in other manners.

FIG. 10 shows axial distance mask 1060. As used herein, "axial" refers to a dimension between the probe and pixels in ultrasound image data 1000. Axial distance mask 1060 may be determined by processor 320, for example, using ROI location processor 326. As shown, axial distance mask 1060 corresponds to segmented liver 1010. As the distance from the probe grows larger, the intensity of pixels in axial distance mask 1060 decrease in intensity, although not necessarily proportionally. Axial distance mask 1060 may adjust pixel values (depth values) based on their distance from a reference point (e.g., liver capsule or skin surface). Axial distance mask 1060 may be used to emphasize or de-emphasize specific regions of the image based on their proximity to the reference point. Axial distance mask 1060 may be created in the following exemplary fashion. First, for pixels located in a first region (e.g., 0 to 1 cm from the liver capsule), values are set to 0 (i.e., black). This filters out these pixels, making the area immediately proximate to the liver capsule unsuitable for ROI placement. Second, for pixels in a second region (e.g., between 1 cm and 1.5 cm from the liver capsule), their values are gradually increased from 0 to 1. This creates a smooth transition from the masked area around the liver capsule to the subsequent region. Third, for pixels in a third region (e.g., between 1.5 cm and 7 cm from the liver capsule), their values are set to 1 (i.e., white). This highlights and emphasizes the area within this distance range, making it the primary area of interest for further analysis or processing. Fourth, for pixels located in a fourth region (e.g., greater than 7 cm or from the skin), their values are gradually decayed from 1 to 0. This fading effect may help to deemphasize regions that are farther away from the skin surface, directing the focus to areas closer to the liver capsule. Axial distance mask 1060 may be combined with other masks as described herein to determine a location for a region of interest. Axial distance mask 1060 tends to give more weight to locations proximate the probe in the liver. In other words, axial distance mask 1060 increases the chances that a region of interest will be located proximate the probe, as shown. A shallower depth may be preferable for shear-wave elastography measurements, as such measurements may be affected by depth of the target tissue and the distance to the target tissue. By emphasizing or de-emphasizing specific regions of the image based on their proximity to the reference point (e.g., liver capsule or skin surface), axial distance mask 1060 can help to improve the accuracy and reliability of shear-wave elastography measurements by directing the focus to areas closer to the liver capsule where the measurements may be more reliable. Axial distance mask 1060 may be generated based on the entire segmented liver 1010 or portions that have not been filtered out by poor-probe-contact mask 1030.

FIG. 11 shows lateral distance mask 1070. Lateral distance mask 1070 may be similar in respects to axial distance mask 1060. As used herein, "lateral" refers to a horizontal dimension in ultrasound image data 1000. Lateral distance mask 1070 may be determined by processor 320, for example, using ROI location processor 326. As shown, lateral distance mask 1070 corresponds to segmented liver 1010. As the distance from the center line of segmented liver 1010 or centerline of ultrasound image data 1000 increases, the intensity of pixels in lateral distance mask 1070 decrease in intensity, although not necessarily proportionally. Lateral distance mask 1070 may be generated in the following exemplary fashion. Initially, the central line of ultrasound image data 1000 is identified. From there, distances between this centerline and every other point in ultrasound image data 1000 are calculated. These distances are then used to create a mask, where the intensity of each pixel corresponds to its distance from the centerline. Pixels closer to the centerline in lateral distance mask 1070 have a higher intensity, while those farther from the centerline have a lower intensity. This decrease in intensity follows a linear decay, creating a gradient effect, with the maximum intensity at the centerline and a uniform linear decay towards the edges. Lateral distance mask 1070 will be combined with other masks as described herein to determine a location for a region of interest. Lateral distance mask 1070 tends to give more weight to locations proximate the centerline of segmented liver 1010 or centerline of ultrasound image data 1000. In other words, lateral distance mask 1070 increases the chances that a region of interest will be located proximate the centerline, as shown. The centerline region of ultrasound image data 1000 may result from more consistent and reliable acoustic properties. This is because the centerline of ultrasound image data 1000 is often where the ultrasound beam is most focused and where there is less attenuation of the sound waves. Additionally, placing the region of interest towards the center of the image may help minimize the impact of artifacts or other sources of interference that may be more common towards the edges of the image (e.g., ribs). Lateral distance mask 1070 may be generated based on the entire segmented liver 1010 or portions that have not been filtered out by poor-probe-contact mask 1030.

Figure 12:
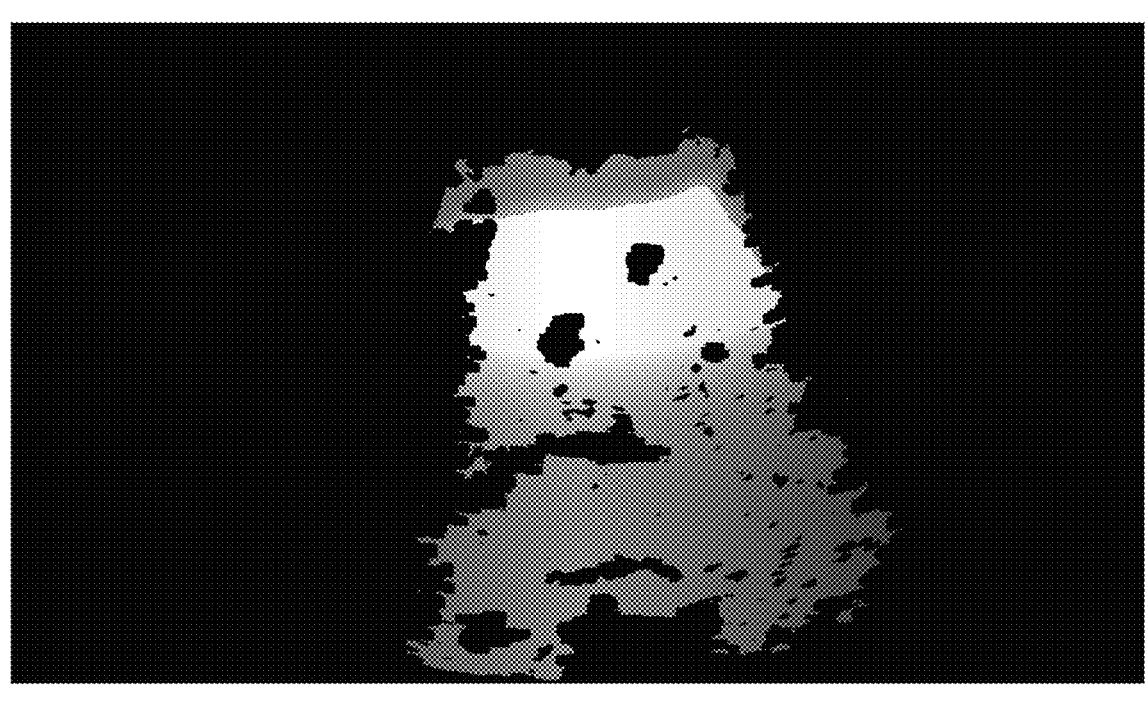
FIG. 12 shows a mask combination, according to embodiments.

FIG. 12 shows a mask combination 1080 of liver tissue mask 1050, axial distance mask 1060, and lateral distance mask 1070. Mask combination 1080 may be determined by processor 320, for example, using ROI location processor 326. According to an embodiment, liver tissue mask 1050 is multiplied with axial distance mask 1060, and lateral distance mask 1070 is added. Further, poor-probe-contact mask 1030 has already been incorporated as part of the liver tissue mask 1050 generation. Poor-probe-contact mask 1030 may be multiplied with other masks as part of the combination process. According to an embodiment, liver tissue mask 1050 is multiplied with both axial distance mask 1060 and poor probe contact mask 1030, and lateral distance mask 1070 is added.

Figure 13:
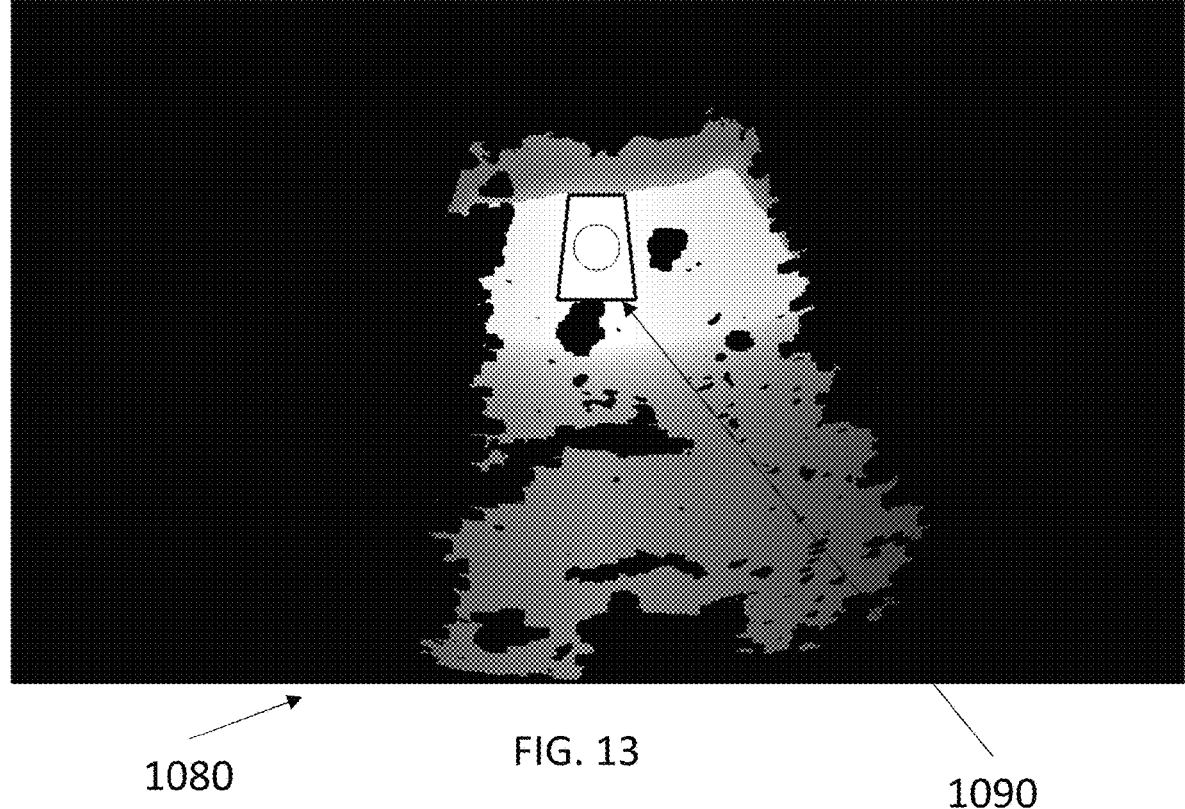
FIG. 13 shows a mask combination with an identified area for placing a region of interest, according to embodiments.

As shown in FIG. 13, the brighter area in mask combination 1080 represents an area in the liver that is preferred or identified for placing region of interest 1090, as shown in FIG. 13. Automatic identification for placement of region of interest 1090 may be determined by processor 320, for example, using ROI location processor 326. Region of interest 1090 may include one or more regions of interest. The region of interest 1090 may identify an area in the liver from which to track the propagation of shear waves as part of a shear-wave elastography process, for example, to assess stiffness of the liver at that location. As shown region of interest 1090 includes a trapezoidal region of interest and a circular region of interest. The trapezoidal region of interest may be for measuring liver stiffness across a broader region of the liver to provide a more comprehensive assessment of potential hepatic fibrosis, although it may be more susceptible to the inclusion of artifacts (e.g., blood vessels) due to its larger coverage. The circular region of interest may be for more precise measurements of liver stiffness in specific areas, potentially reducing the inclusion of artifacts, to assist in diagnosing hepatic fibrosis. Region of interest 1090 may be automatically placed by processor 320 in mask combination 180, for example, according to the size of region of interest 1090 and available areas in mask combination 1080. In addition or as an alternative, the operator may choose a suitable location for region of interest 1090. For example, processor 320 may automatically pick an area for region of interest 1090 in ultrasound image data 1000, and present it on display 330. The operator may then interact through user input 340 (e.g., mouse or touchscreen) to indicate to processor 320 the desired region of interest 1090 location. For example, the operator may agree with the automatic placement of region of interest 1090 and indicate so through user input 340. As an alternative, the operator may choose a different location for region of interest 1090. For example, the operator may drag and drop region of interest 1090 using user interface 340. Such a drag-and-drop operation may be viewable in real-time on display 330. As another option, processor 320 may automatically determine possible areas for placement of region of interest 1090 and cause this to be presented on display 330. The operator may then select a location for region of interest 1090 from the possible areas through interaction with user input 340. While FIG. 13 shows region of interest 1090 on mask combination 1080, region of interest 1090 (or possible areas for region of interest 1090), as described above, may be presented on ultrasound image data 1000 (i.e., not just the masked portion of ultrasound image data 1000).

Figure 14:
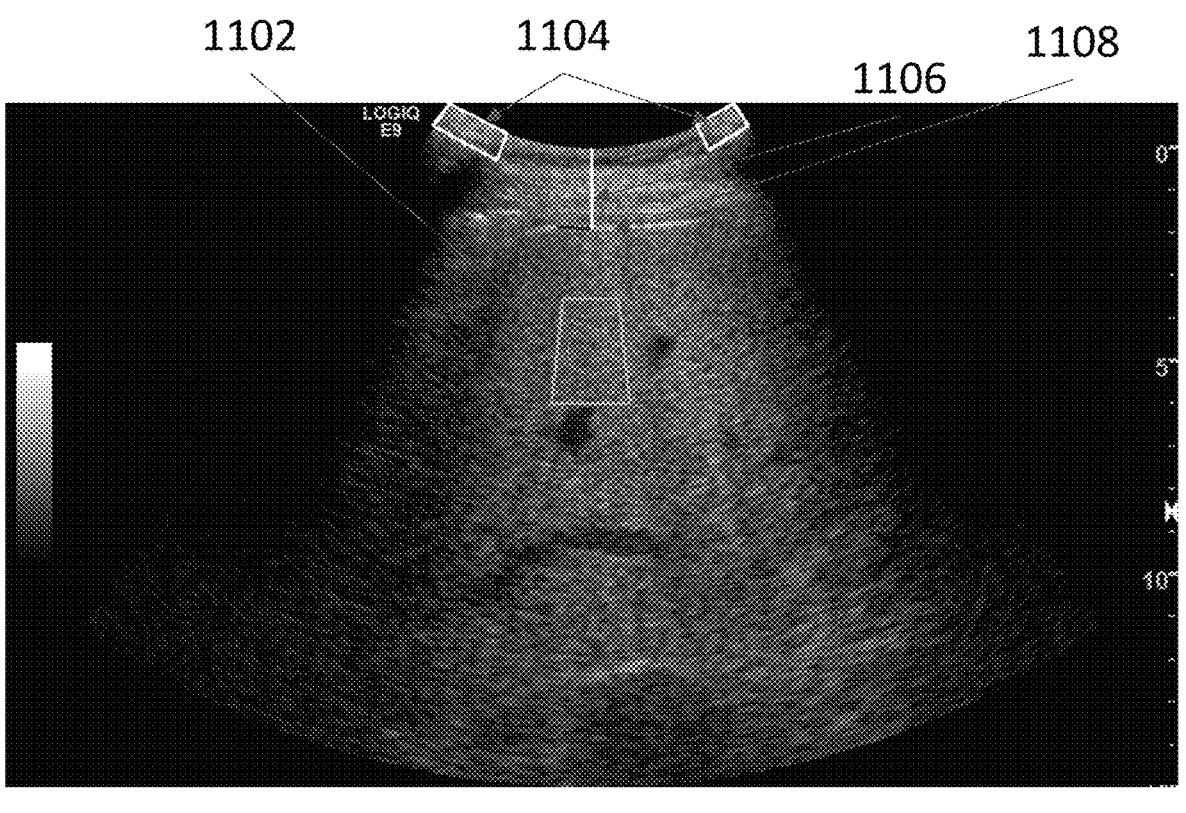
FIG. 14 shows a presentation of ultrasound image data with indicators, according to embodiments.

FIG. 14 shows a presentation 1100 of ultrasound image data 1000 with various indicators 1102, 1104, 1106, 1108. Processor 320 may cause presentation 1100 to be presented on display 330, including indicators 1102, 1104, 1106, 1108 and any updates (e.g., real-time updates). Indicator 1102 is for a region of interest, and may be similar to region of interest 1090. The operator may be able to move region-of-interest indicator 1102 around on presentation 1100 through user interface 340.

Figure 16:
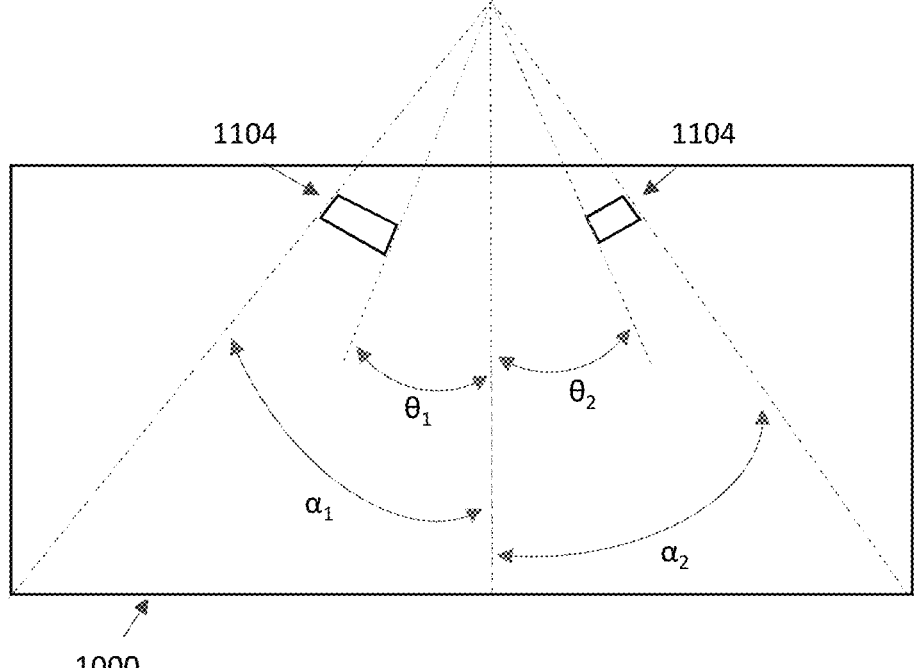
FIG. 16 illustrates techniques for generating poor-probe-contact indicators, according to embodiments.

Indicator(s) 1104 may indicate locations at which there is poor probe contact with the patient. Indicators 1104 may change in real-time in response to movements in the probe or the patient. Indicators 1104 may change sizes based on an area in which there is poor probe contact. Indicators 1104 may disappear altogether (on one or both sides) if contact is improved. FIG. 16 illustrates an embodiment as to how poor-probe-contact indicator(s) 1104 may be generated. As shown in FIG. 8, for example, poor-probe-contact artifacts may be identified in poor-probe-contact artifact mask 1040.

If an artifact exists, then a corresponding indicator 1104 is determined. If an artifact is identified on the right side, then an indicator 1104 is determined for the right. If an artifact is identified on the left side, then an indicator 1104 is determined for the left. Indicators 1104 may not be determined when there is no artifact identified.

As shown in FIG. 16, indicators 1104 can be determined for the left side and the right side for presentation with ultrasound image data 1000. Indicators 1104 are shown as trapezoids, although other shapes may be suitable. The heights of the trapezoids may be any suitable height. For example, the heights may correspond to the thickness between the epidermis and the liver capsule, as shown in FIG. 14. The width or orientation of the sides of indicators 1104 may be determined as follows. For each indicator 1104, an angle $\alpha$ and angle $\theta$ may be determined with respect to the centerline of ultrasound image data 1000 or with respect to some other reference. As shown, $\alpha_1$ and $\theta_1$ correspond to the left-side indicator 1104 and $\alpha_2$ and $\theta_2$ correspond to the right-side indicator 1104. Angle $\alpha_1$ and $\alpha_2$ may or may not be identical, as may be $\theta_1$ and $\theta_2$. The discussion herein will only be for one angle $\alpha$ and one angle $\theta$, although two or even more may be possible. The sides of indicators 1104 may exactly match lines determined by the angles, or may otherwise bear some relationship or correspond to lines determined by the angles, or just the angles.

Angle $\alpha$ may be determined by identifying a farthest lateral point on ultrasound image data 1000 that the probe can reach (for example, left-most line or right-most line in FIG. 16). Then a line may be drawn to an inferred location of ultrasound transducer (convergence of lines in FIG. 16). Angle $\alpha$ may be determined from this line as compared to the centerline of ultrasound image data 1000, or some other reference, such as a vertical line extending through the inferred location of the ultrasound transducer.

Figure 17:
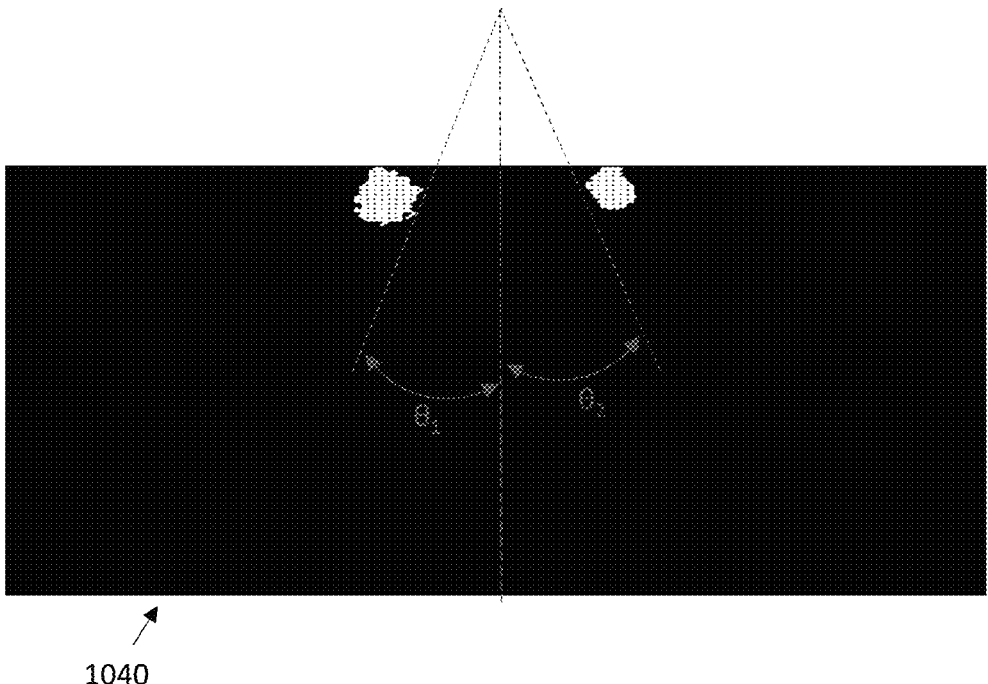
FIG. 17 illustrates techniques for determining an extent of poor-probe contact image data, according to embodiments.

Angle $\theta$ may be identified within the range of angle $\alpha$ (angle $\theta$ may be less than angle $\alpha$). FIG. 17 is illustrative of embodiments. Poor-probe-contact artifact mask 1040 from FIG. 8 is shown. Poor-probe-contact artifact mask 1040 has two segments. A line may be drawn from an inferred location of ultrasound transducer to an innermost location of a given segment (or a location corresponding to the innermost location of a given segment). That line may determine angle $\theta$. In the example shown in FIG. 17, a first angle $\theta_1$ is determined by drawing a line from the inferred location of ultrasound transducer to the innermost location of the left-side segment of poor-probe-contact artifact mask 1040. A second angle $\theta_2$ is determined by drawing a line from the inferred location of ultrasound transducer to the innermost location of the right-side segment of poor-probe-contact artifact mask 1040. Angles $\theta_1$ and $\theta_2$ may be used to determine indicators 1104 and/or poor-probe-contact mask 1030, as discussed above.

Going back to FIG. 14, indicator 1106 indicates a distance between the patient's epidermis and the liver capsule or liver. The upper extent of the liver or liver capsule may be determined by segmentation, as discussed above. Indicator 1106 may be a measurement in length, for example, in millimeters. The length of this distance may be an indicator of a patient's condition or measurement, such as body-mass index. The actual distance in units may also be displayed on presentation 1100 (not shown).

Indicator 1108 indicates an angular, spatial relationship between the orientation of the probe and the patient's liver. This relationship may be relative, and not determinative of the angles of the probe and/or liver with respect to some other reference (e.g., the table). For example, the angular, spatial relationship may be determined in part by the shape and orientation of segmented liver 1010. Better data (for example, clearer and more accurate data) may be obtained if the probe is substantially parallel to the patient's liver. The angular, spatial relationship between the orientation of the probe and liver may be performed in the following manner. The slope of the liver capsule is determined by selecting a number of points (e.g., three points) along this capsule: one at the center, and two others a fixed distance to the left and right of the center. Lines connecting these points form two angles, one between the center and right point and the other between the center and left point. The slope of the liver capsule is then obtained by averaging these two angles. This slope is compared to a predefined threshold (e.g., 5 degrees). If the slope is larger than this threshold, a clockwise adjustment of the probe's angle is recommended. If the slope is less than the negative of this threshold, an anticlockwise adjustment is recommended. If the slope falls within (−5,+5), no adjustment is suggested. Indicator 1108 may indicate to the operator whether the probe should be adjusted, angularly, in order to better match the orientation of the probe with the orientation of the patient's liver. Indicator 1108 may change in real-time, due to movements in the probe and/or patient.

It will be understood by those skilled in the art that various changes may be made and equivalents may be substituted without departing from the scope of the novel techniques disclosed in this application. In addition, many modifications may be made to adapt a particular situation or material to the teachings of the novel techniques without departing from its scope. Therefore, it is intended that the novel techniques not be limited to the particular techniques disclosed, but that they will include all techniques falling within the scope of the appended claims.

The invention claimed is:

1. A method comprising:
   receiving ultrasound image data of a patient, including a segmented region corresponding to a liver;
   prior to performing shear-wave elastography, automatically identifying an area for a region of interest within the segmented region using at least one mask, wherein the region of interest corresponds to a region in the liver for subsequently performing shear-wave elastography; and
   presenting, on a display, the ultrasound image data and the area for the region of interest,
   wherein said automatically identifying the area for the region of interest within the segmented region using the at least one mask further comprises:
      determining a first mask by filtering pixels that do not correspond to liver tissue;
      determining a second mask for identifying an axial position in the segmented region;
      determining a third mask for identifying a lateral position in the segmented region;
      combining the first mask, the second mask, and the third mask to limit the area for the region of interest within the segmented region;
      determining a fourth mask corresponding to image data in a region resulting from poor probe contact with the patient; and
      combining the first mask, the second mask, the third mask, and the fourth mask to limit the area for the region of interest within the segmented region.

2. The method of claim 1, further comprising segmenting the ultrasound image data to form the segmented region.

3. The method of claim 1, wherein the at least one mask filters out pixels corresponding to at least one blood vessel in the liver.

4. The method of claim 1, wherein the at least one mask filters out pixels corresponding to at least one hyperechoic region in the liver.

5. The method of claim 1, further comprising performing shear-wave elastography to receive elasticity information from the region of interest in the liver.

6. The method of claim 1, further comprising:

determining, in real-time, an angular, spatial relationship between the segmented region and an ultrasound probe; and presenting, on the display, a dynamic, real-time indicator corresponding to the angular, spatial relationship between the segmented region and the ultrasound probe.

7. An ultrasound imaging system comprising:

a probe including at least one transducer configured to transmit ultrasonic waves and receive reflected ultrasonic waves;

a display configured to present a presentation to an operator; and a processor configured to process data corresponding to the reflected ultrasonic waves to determine a segmented region corresponding to a liver of a patient, and further configured to cause the display to present the presentation, wherein the presentation includes image data of the segmented region and at least one dynamic region-of-interest indicator indicating a corresponding region of interest in the liver for subsequently performing shear-wave elastography, wherein the processor is configured to automatically determine the region of interest within the segmented region using at least one mask prior to performing shear-wave elastography, wherein the processor is further configured to automatically determine the region of interest from the segmented region using the at least one mask by:

determining a first mask by filtering pixels that do not correspond to liver tissue;

determining a second mask for identifying an axial position in the segmented region;

determining a third mask for identifying a lateral position in the segmented region;

combining the first mask, the second mask, and the third mask to limit an area for the region of interest within the segmented region;

determining a fourth mask corresponding to image data in a region resulting from poor probe contact with the patient; and combining the first mask, the second mask, the third mask, and the fourth mask to limit the area for the region of interest within the segmented region.

8. The ultrasound imaging system of claim 7, further comprising a user interface, wherein the processor is configured to receive data from the user interface indicating a final location for the region of interest.

9. The ultrasound imaging system of claim 7, wherein the at least one mask filters out pixels that correspond to at least one blood vessel in the liver.

10. The ultrasound imaging system of claim 7, wherein the at least one mask filters out pixels that correspond to at least one hyperechoic region in the liver.

11. The ultrasound imaging system of claim 7, wherein the presentation further includes an indicator of poor probe contact.

12. The ultrasound imaging system of claim 7, further comprising a shear-wave generator external to the probe to generate ultrasonic shear waves in the region of interest.

13. The ultrasound imaging system of claim 7, wherein the processor is further configured to:

determine, in real-time, an angular, spatial relationship between the segmented region and an ultrasound probe; and include, in the presentation, a dynamic indicator indicating, in real-time, the angular, spatial relationship between the segmented region and the ultrasound probe.

\* \* \* \* \*